United States Patent
Meade et al.

(10) Patent No.: US 9,138,237 B2
(45) Date of Patent: Sep. 22, 2015

(54) TOTAL JOINT INSTRUMENTATION AND METHOD FOR USE

(71) Applicant: Arthrex, Inc., Naples, FL (US)

(72) Inventors: Thomas Daniel Meade, Allentown, PA (US); Michael James Joyce, Emmaus, PA (US); Gary Scott Sherman, Naples, FL (US)

(73) Assignee: Arthrex, Inc., Naples, FL (US)

( * ) Notice: Subject to any disclaimer, the term of this patent is extended or adjusted under 35 U.S.C. 154(b) by 256 days.

(21) Appl. No.: 13/650,720

(22) Filed: Oct. 12, 2012

(65) Prior Publication Data

US 2013/0096563 A1 Apr. 18, 2013

Related U.S. Application Data

(60) Provisional application No. 61/546,731, filed on Oct. 13, 2011.

(51) Int. Cl.
*A61B 17/15* (2006.01)
*A61B 17/17* (2006.01)

(52) U.S. Cl.
CPC .............. *A61B 17/154* (2013.01); *A61B 17/15* (2013.01); *A61B 17/155* (2013.01); *A61B 17/157* (2013.01); *A61B 17/17* (2013.01); *A61B 17/1764* (2013.01)

(58) Field of Classification Search
CPC .... A61B 17/15; A61B 17/154; A61B 17/155; A61B 17/157; A61B 17/17; A61B 17/1764
USPC ........................ 606/86 R, 87–88, 90, 96–98
See application file for complete search history.

(56) References Cited

U.S. PATENT DOCUMENTS

| | | | |
|---|---|---|---|
| 4,524,766 A | | 6/1985 | Petersen |
| 4,938,762 A | * | 7/1990 | Wehrli ............................ 606/88 |
| 5,395,376 A | * | 3/1995 | Caspari et al. .............. 606/86 R |
| 5,788,700 A | | 8/1998 | Morawa et al. |
| 6,478,799 B1 | * | 11/2002 | Williamson .................... 606/90 |
| 6,613,052 B1 | | 9/2003 | Kinnett |
| 7,104,996 B2 | * | 9/2006 | Bonutti ....................... 606/86 R |
| 8,419,740 B2 | * | 4/2013 | Aram et al. .................... 606/88 |
| 8,974,459 B1 | | 3/2015 | Axelson, Jr. et al. |
| 2005/0143746 A1 | * | 6/2005 | Steffensmeier et al. ........ 606/88 |
| 2009/0043309 A1 | * | 2/2009 | Rasmussen .................... 606/88 |
| 2009/0043310 A1 | | 2/2009 | Rasmussen |
| 2009/0087276 A1 | | 4/2009 | Rose |
| 2009/0287216 A1 | * | 11/2009 | Warkentine et al. ............ 606/87 |
| 2015/0045801 A1 | | 2/2015 | Axelson, Jr. et al. |

FOREIGN PATENT DOCUMENTS

WO 0166021 A1 9/2001

OTHER PUBLICATIONS

European Search Report for Application No. EP 12 18 8387 dated Dec. 10, 2012.
"Kinematic Alignment in Total Knee Arthroplasty," Chapter 121, by Stephen M. Howell and Maury L. Hull, pp. 1255-1268, e121-1, Aug. 3, 2011.

* cited by examiner

*Primary Examiner* — Larry E Waggle, Jr.
(74) *Attorney, Agent, or Firm* — Carlson, Gaskey & Olds

(57) ABSTRACT

A total joint instrument set according to an exemplary aspect of the present disclosure includes, among other things, a guide assembly that orients a cut in a first bone and a linkage guide that orients a cut in a second bone. A positioning of the linkage guide is mechanically linked to at least a portion of the guide assembly.

18 Claims, 41 Drawing Sheets

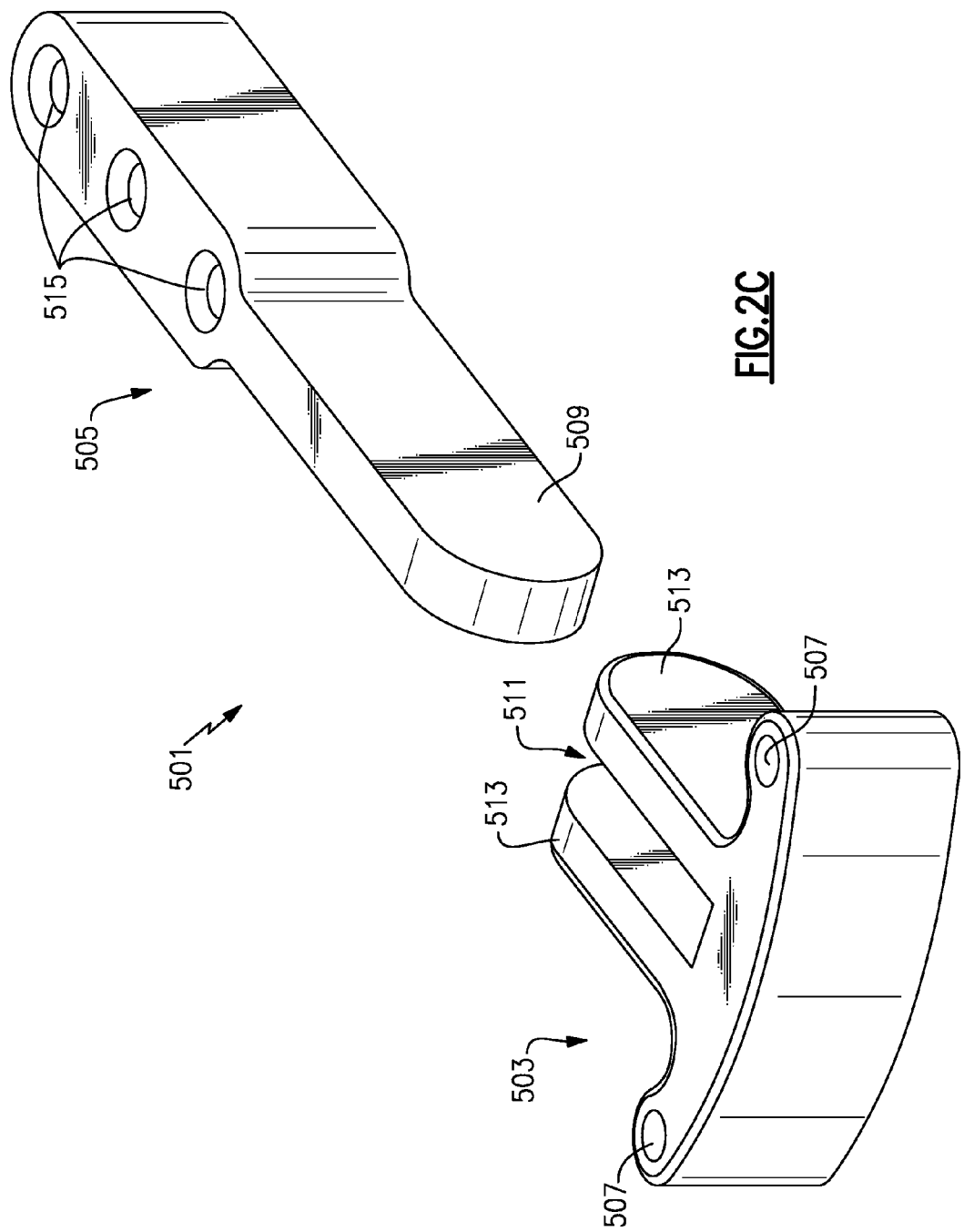

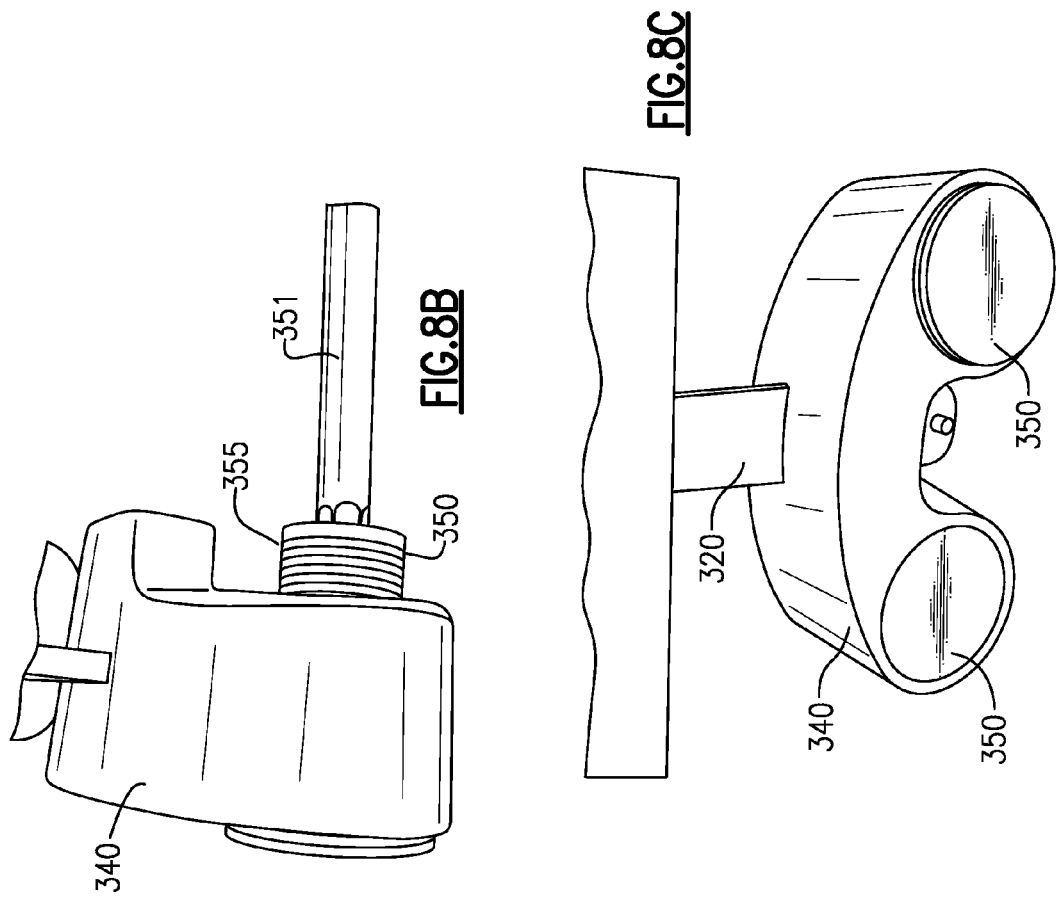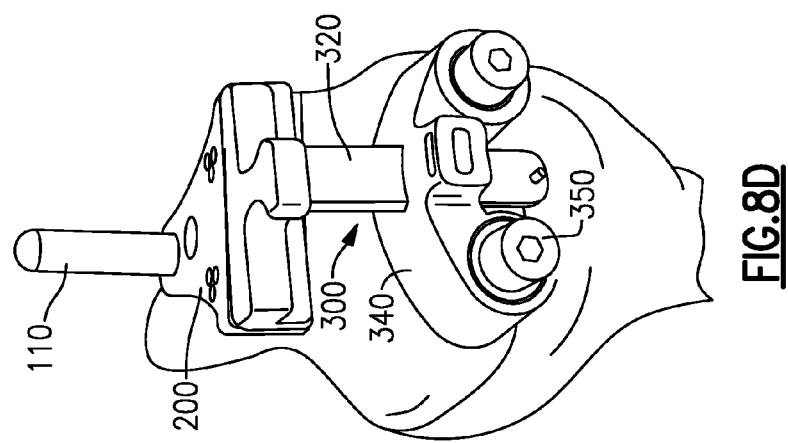

TOTAL JOINT INSTRUMENTATION AND METHOD FOR USE

CROSS REFERENCE TO RELATED APPLICATION

This application claims priority to U.S. Provisional Application No. 61/546,731, filed Oct. 13, 2011.

BACKGROUND

This disclosure relates to orthopedic surgical instrumentation, and more particularly to a total joint instrument set and method for using the same to prepare for the implantation of a total joint implant.

Arthroplasty is an orthopedic surgical procedure performed to repair diseased joints. For example, total knee arthroplasty (TKA), or total knee replacement surgery, has been performed for many years to treat patients with diseased knee joints.

Existing total joint instrumentation can be cumbersome to use, difficult to assemble and can only be used to make cuts that are based on an estimation of an appropriate angle and rotation relative to an assumed mechanical axis of a normal joint. The result is a reconstruction that may not match the patient's original anatomy pre-disease.

SUMMARY

A total joint instrument set according to an exemplary aspect of the present disclosure includes, among other things, a guide assembly that orients a cut in a first bone and a linkage guide that orients a cut in a second bone. A positioning of the linkage guide is mechanically linked to at least a portion of the guide assembly.

In a further non-limiting embodiment of the foregoing total joint instrument set, the guide assembly includes a femoral alignment guide, a cutting block and a varus/valgus alignment guide.

In a further non-limiting embodiment of either of the forgoing total joint instrument sets, the cutting block is rotatable about a connecting rod of the femoral alignment guide.

In a further non-limiting embodiment of any of the foregoing total joint instrument sets, the varus/valgus alignment guide includes a connecting surface that is magnetically connectable to a cutting surface of the cutting block.

In a further non-limiting embodiment of any of the foregoing total joint instrument sets, the linkage guide includes a yoke and a linkage bar received by the yoke.

In a further non-limiting embodiment of any of the foregoing total joint instrument sets, the linkage guide includes a cutting block and a linkage bar received by the cutting block.

In a further non-limiting embodiment of any of the foregoing total joint instrument sets, the cutting block includes a slot and a spring mounted within a recess of the slot that removably retains the linkage bar within the slot of the cutting block.

In a further non-limiting embodiment of any of the foregoing total joint instrument sets, a slope indicator is removably connected to the cutting block to adjust an anterior/posterior slope alignment in the second bone.

In a further non-limiting embodiment of any of the foregoing total joint instrument sets, a marking template aligns the cut in the first bone with the cut in the second bone.

In a further non-limiting embodiment of any of the foregoing total joint instrument sets, the linkage guide is mechanically linked to at least one guide pin of the guide assembly.

A method of preparing a joint for implantation of a total joint implant, according to another exemplary aspect of the present disclosure includes, among other things, positioning a first cutting block relative to a first bone of the joint. A minimum depth of a cut in a second bone is estimated by referencing the positioning of the first cutting block. A second cutting block is positioned relative to the estimate of the minimum depth of the cut in the second bone. Cuts in the first bone and the second bone are made by using the first cutting block and the second cutting block.

In a further non-limiting embodiment of the foregoing method of preparing a joint for implantation of the total joint implant, the step of positioning the first cutting block includes matching a pre-disease anatomy of the joint.

In a further non-limiting embodiment of either of the foregoing methods of preparing a joint for implantation of the total joint implant, the step of estimating includes marking the second bone with a line that denotes the minimum depth of the cut in the second bone.

In a further non-limiting embodiment of any of the foregoing methods of preparing a joint for implantation of the total joint implant, a marking template is used during the step of marking.

In a further non-limiting embodiment of any of the foregoing methods of preparing a joint for implantation of the total joint implant, the method includes magnetically connecting the marking template to the first cutting block.

In a further non-limiting embodiment of any of the foregoing methods of preparing a joint for implantation of the total joint implant, the step of positioning the second cutting block includes mechanically linking the second cutting block to at least one guide pin that connects the first cutting block to the first bone.

In a further non-limiting embodiment of any of the foregoing methods of preparing a joint for implantation of the total joint implant, the method includes making anterior, posterior and chamfer cuts in the first bone with a third cutting block.

In a further non-limiting embodiment of any of the foregoing methods of preparing a joint for implantation of the total joint implant, the method includes positioning the second cutting block, positioning a linkage bar within a slot of the second cutting block and retaining the linkage bar within the slot of the second cutting block with a spring.

In a further non-limiting embodiment of any of the foregoing methods of preparing a joint for implantation of the total joint implant, the method includes adjusting an anterior/posterior slope alignment of the second bone prior to the step of making cuts in the second bone.

In a further non-limiting embodiment of any of the foregoing methods of preparing a joint for implantation of the total joint implant, the method includes estimating a size of the total joint implant using an alignment guide.

The various features and advantages of this disclosure will become apparent to those skilled in the art from the following detailed description. The drawings that accompany the detailed description can be briefly described as follows.

BRIEF DESCRIPTION OF THE DRAWINGS

FIG. 2C illustrates yet another example linkage guide.

FIGS. 6, 7, 8A, 8B, 8C, 8D, 9A, 9B, 10, 11, 12A, 12B, 12C, 13A, 13B, 13C, 14, 15A and 15B illustrate an example implementation of the orthopedic surgical instrumentation depicted by FIGS. 1-5 for making various cuts in a patient's joint to prepare the patient for the implantation of a total joint implant.

DETAILED DESCRIPTION

FIGS. 1-5 illustrate various orthopedic surgical instruments that can be used to prepare a patient for the implantation of a total joint implant, such as during an arthroplasty procedure. In one example, the orthopedic surgical instruments are part of a total joint instrument set that can be used to prepare a patient's tibia and femur, such as by sizing, marking and making numerous cuts in the tibia and femur, for implantation of a total knee implant. However, the illustrated instruments are not limited to uses associated with the tibia and femur and could have additional applications for preparing for the implantation of any total joint implant or any other surgery.

Figure 1A:
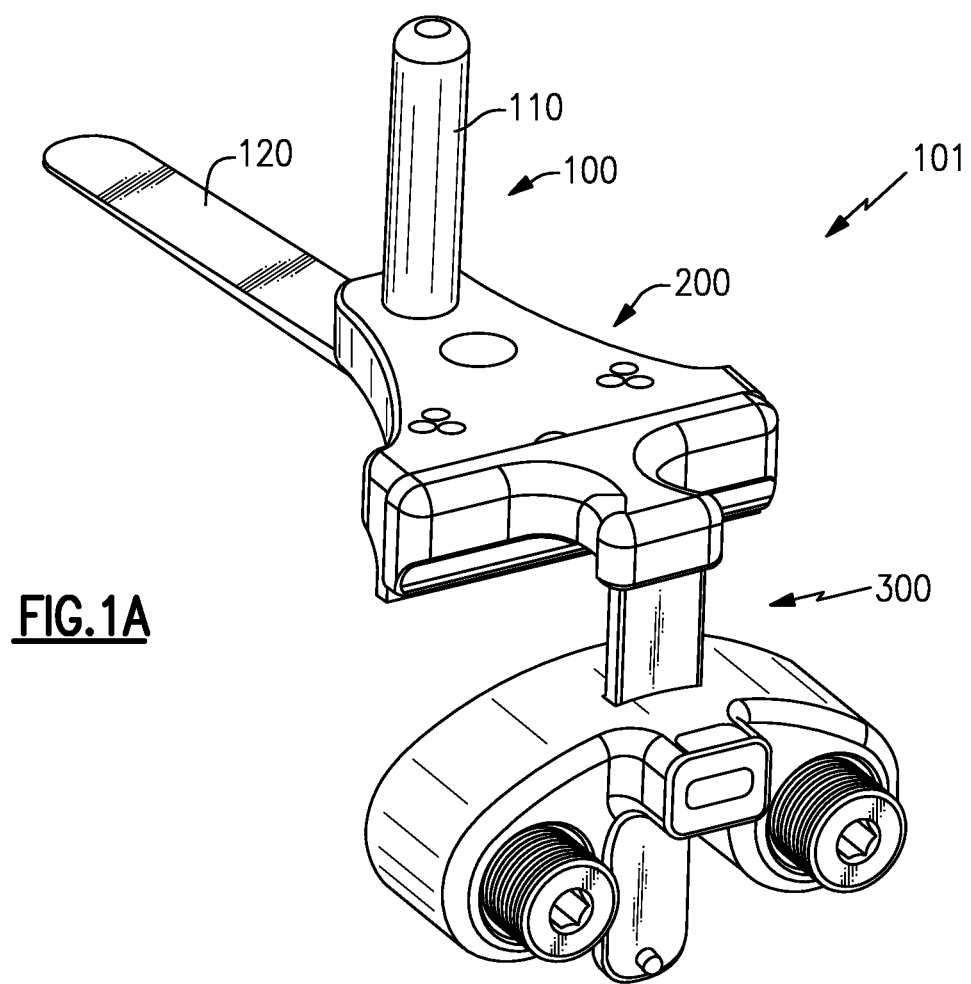
FIG. 1A illustrates a guide assembly including an extramedullary femoral alignment guide, a femoral cutting block and an adjustable varus/valgus alignment guide for making femoral cuts in a patient.
Figure 1B:
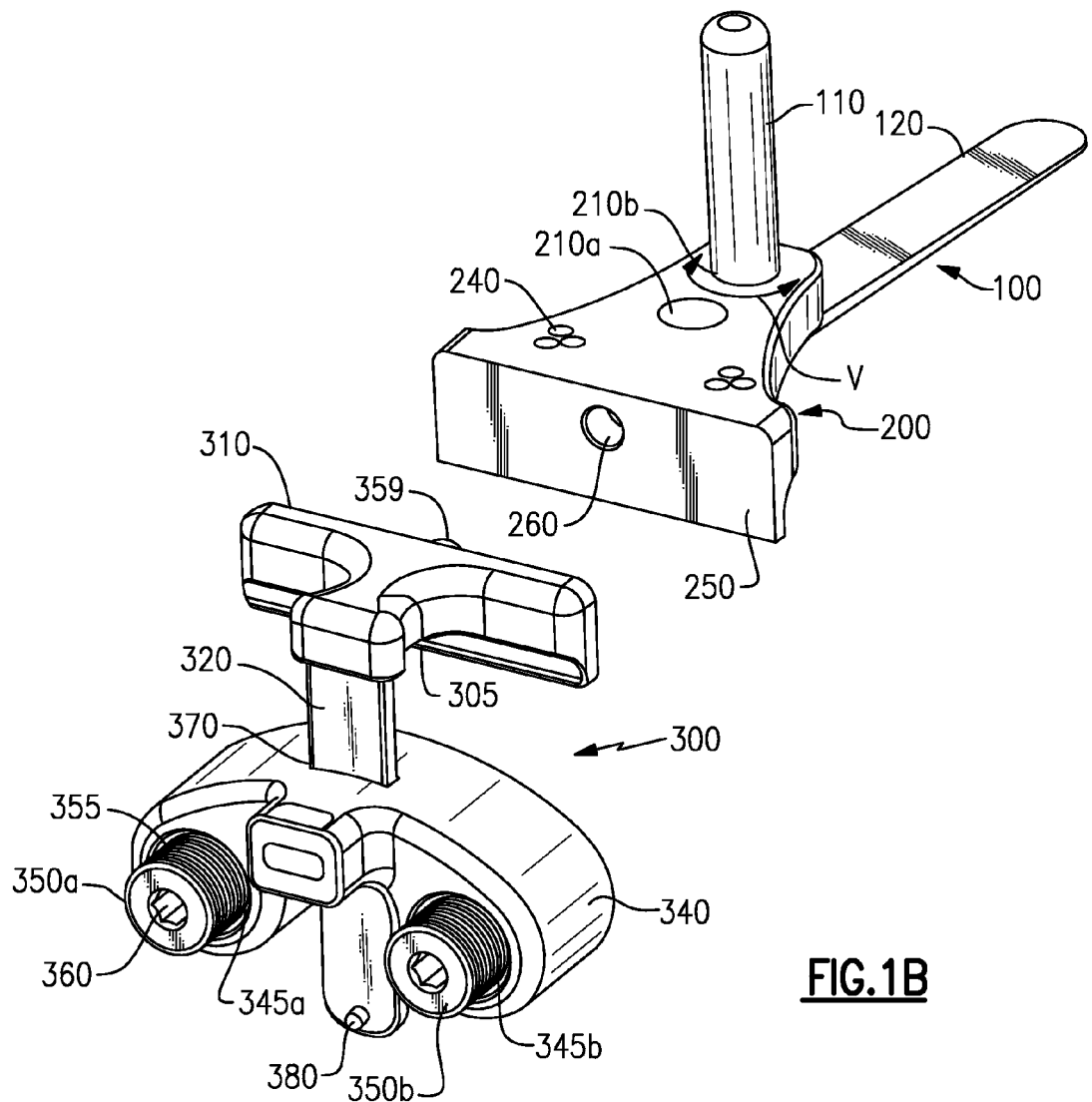
FIG. 1B is an exploded view of the assembly of FIG. 1A.

FIGS. 1A and 1B illustrate a guide assembly 101 for orienting and positioning cuts in a first bone, such as femoral cuts in a patient's femur to prepare for the implantation of a total knee implant. The guide assembly 101 includes an extramedullary femoral alignment guide 100, a femoral cutting block 200 and an adjustable varus/valgus alignment guide 300. In one example, the extramedullary femoral alignment guide 100 establishes an L-shaped configuration that includes a connecting rod 110 and an alignment bar 120 that extends from the connecting rod 110. The femoral cutting block 200 is received by the connecting rod 110 of the extramedullary femoral alignment guide 100. The femoral cutting block 200 is adjustably connectable to the extramedullary femoral alignment guide 100 and is configured to releasably connect to the varus/valgus alignment guide 300. In one embodiment, the femoral cutting block 200 and the varus/valgus alignment guide 300 are magnetically coupled, although other coupling mechanisms can be incorporated into the guide assembly 101.

The alignment bar 120 of the extramedullary femoral alignment guide 100 can extend from a base of the connecting rod 110. The alignment bar 120 is sized and shaped to fit against a patient's femur and maintain alignment along the patient's femoral shaft. The femoral cutting block 200 is received over the connecting rod 110 of the extramedullary femoral alignment guide 100 such that the femoral cutting block 200 can rotate in a varus/valgus direction V (i.e., shifting of femur from one condyle to the other to create either a bowed knee or knocked knee configuration) about the connecting rod 110. The femoral cutting block 200 has one or more holes 210a, 210b that provide locational adjustability of the femoral cutting block 200. The actual placement of the femoral cutting block 200 can vary depending upon the configuration of the patient's anatomy, among other factors.

The femoral cutting block 200 additionally includes a cutting surface 250 having a magnetic surface for connection with the adjustable varus/valgus alignment guide 300. In one example, the cutting surface 250 is a planar cutting surface. A plurality of pin holes 240 extend through the femoral cutting block 200 parallel to the cutting surface 250 for placement of guide pins (not shown) into the femoral bone. The cutting surface 250 can include a bore 260 for mating with a corresponding protrusion 359 of the varus/valgus alignment guide 300 to provide additional support for assembling the two components. It should be understood that any releasable connection mechanism can be used to releasably connect the femoral cutting block 200 and the varus/valgus alignment guide 300.

The varus/valgus alignment guide 300 includes a base 305 having a connecting surface 310 and a protrusion 359 for connecting to the cutting surface 250 of the femoral cutting block 200. A connecting element 320 extends from the base 305 and couples a guide portion 340 to the varus/valgus alignment guide 300. The guide portion 340 includes a slot 370 or other suitable opening that receives the connecting element 320. The guide portion 340 can longitudinally translate along the connecting element 320. Additionally, the connecting element 320 can include a stop 380, such as a nub or other protrusion, to prevent the guide portion 340 from becoming disengaged from the base 305.

Figure 1C:
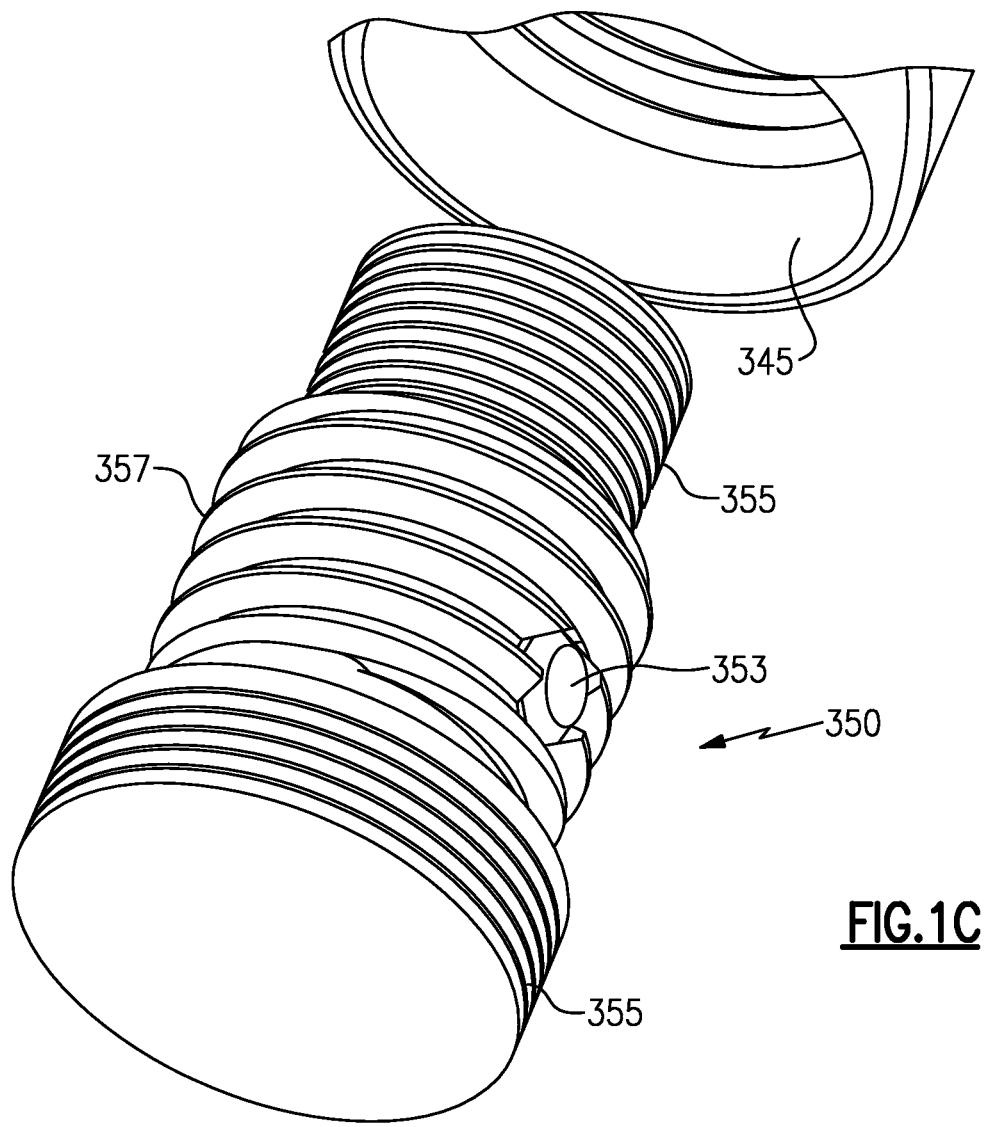
FIG. 1C illustrates an adjustable cylinder of the adjustable varus/valgus alignment guide of FIG. 1A.
Figure 1D:
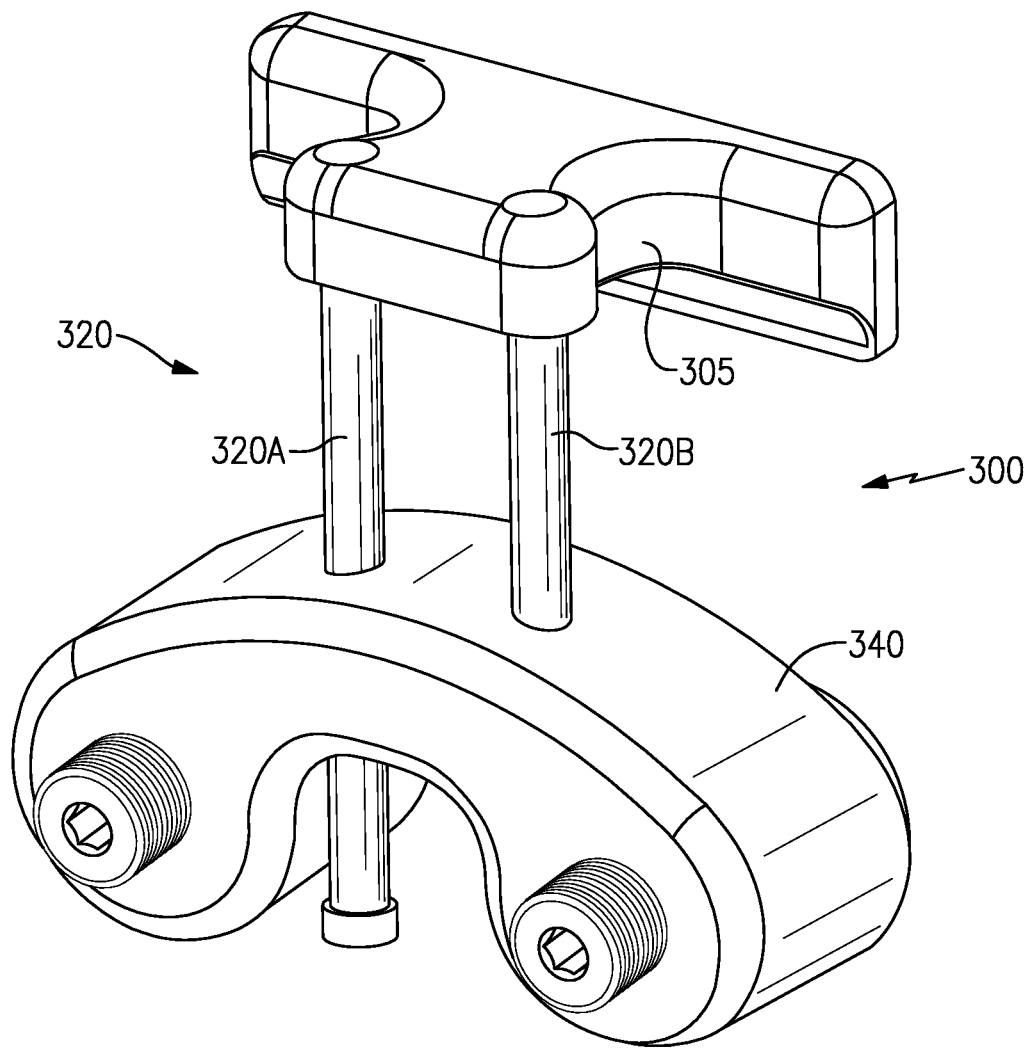
FIG. 1D illustrates another example varus/valgus alignment guide.

In another embodiment, the varus/valgus alignment guide 300 includes a connecting element 320 having a pair of spaced apart legs 320A and 320B that extend from the base 305 and couple the guide portion 340 to the varus/valgus alignment guide 300 (see FIG. 1D). The pair of spaced apart legs 320A, 320B may provide a sturdier and lighter construction as compared to the varus/valgus alignment guide 300 illustrated by FIGS. 1A and 1B.

The guide portion 340 houses independently adjustable varus/valgus alignment cylinders 350a, 350b within openings 345a, 345b. Each cylinder 350a, 350b is adjustable in the anterior/posterior directions and can include discrete markings 355 to indicate the distance each cylinder has been adjusted to reach a desired position relative to the femur of a patient. The adjustment can be made by engaging and manipulating, such as by turning, a driver engagement feature 360 of the cylinders 350a, 350b. In one example, the driver engagement feature 360 is a hex drive, although other drive features could additionally or alternatively be incorporated.

Each cylinder 350a, 350b includes a threaded middle section 357 for moving the cylinder 350a, 350b in the anterior/posterior directions within the openings 345a, 345b of the guide portion 340 (FIG. 1C). The threaded middle section 357 can include a pin 353 positioned on a radially outer surface of the threaded middle section 357 that substantially reduces any unwanted or accidental movement of the cylinder 350a, 350b during the procedure. In one example, the pin 353 includes a nylon material, although other materials are also contemplated.

Figure 2A:
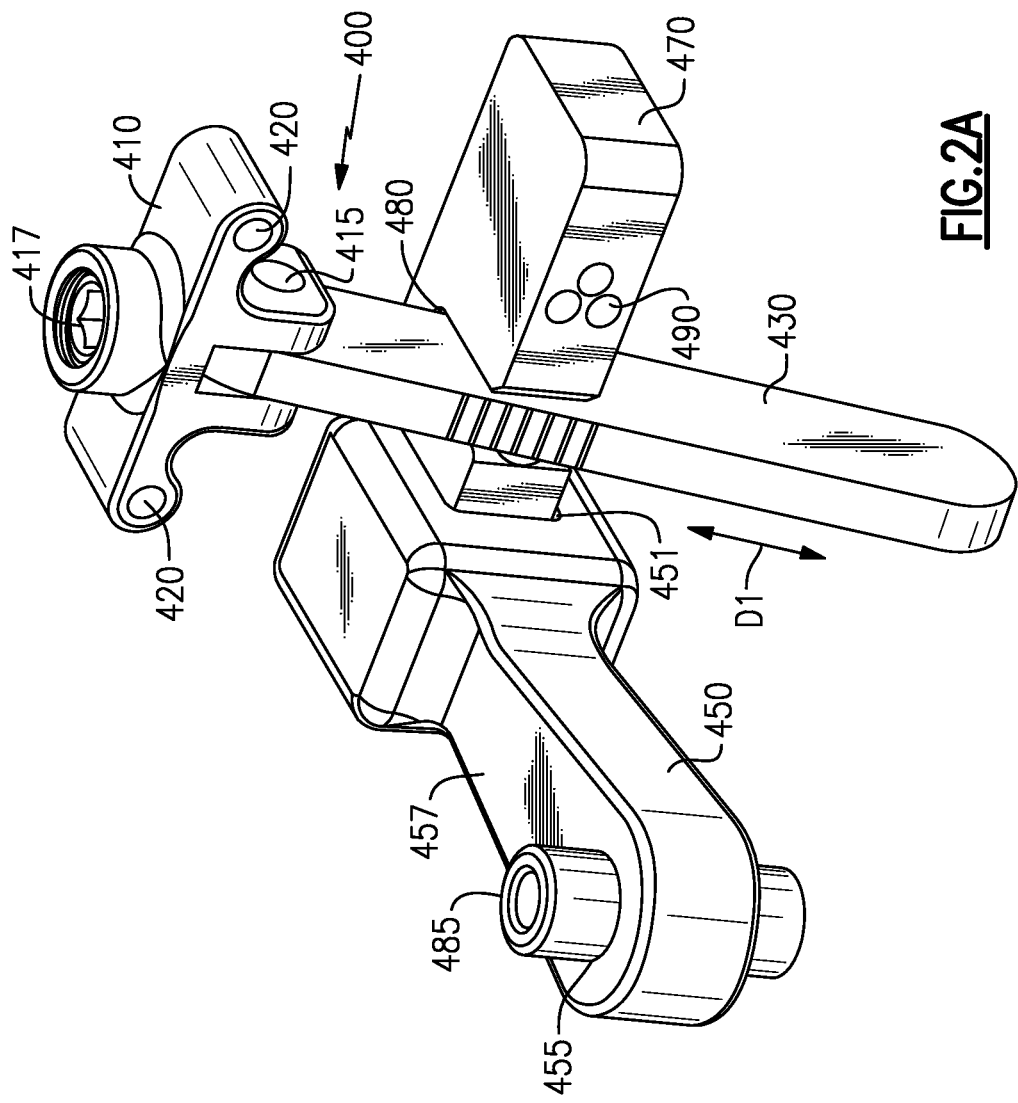
FIG. 2A illustrates a linkage guide having a tibial cutting block and a visual alignment rod for making a tibial cut in a patient.

Additional instrumentation can be used in combination with the guide assembly 101 to prepare a femur and tibia for the implantation of a total knee implant, for example. FIG. 2A illustrates a femoral-tibial linkage guide 400 that is assembled to a tibial cutting block 470 for orienting and positioning cuts in a second bone, such as tibial cuts in the tibia. The femoral-tibial linkage guide 400 includes a yoke 410 and a tibial alignment bar 430. The yoke 410 includes pin holes 420 positioned at on one or both sides of the yoke 410 that are received over femoral guide pins, as is discussed in greater detail below. The tibial alignment bar 430 is connected to the yoke 410 by a pin 415 and can be rotatably adjusted relative to the yoke 410 about the pin 415. The tibial alignment bar 430 can be locked in position by adjusting a locking screw 417.

The tibial cutting block 470 includes a slot 480 that is sized to accommodate the tibial alignment bar 430. The tibial cutting block 470 can be moved in a proximal-distal direction D1 along the tibial alignment bar 430. The tibial cutting block 470 can also be adjusted in the anterior/posterior direction by tilting the tibial cutting block 470 on the tibial alignment bar 430 while maintaining a position parallel to the femur in the varus-valgus direction. Once the tibial cutting block 470 is in a desired position, tibial guide pins (not shown) can be placed through one of the pin holes 490 on each side of the slot 480 in the cutting block.

An optional alignment clamp 450 can be used to visually check the anterior/posterior slope alignment. The alignment clamp 450 has an opening 451, such as a Y-shaped opening, that is sized to receive the tibial cutting block 470. An arm 457 extends from the alignment clamp 450 and includes a through hole 455 that is sized to receive an alignment rod 485 which allows the surgeon to visualize the anterior/posterior slope and perform any necessary adjustments to the positioning of the tibial cutting block 470.

Figure 2B:
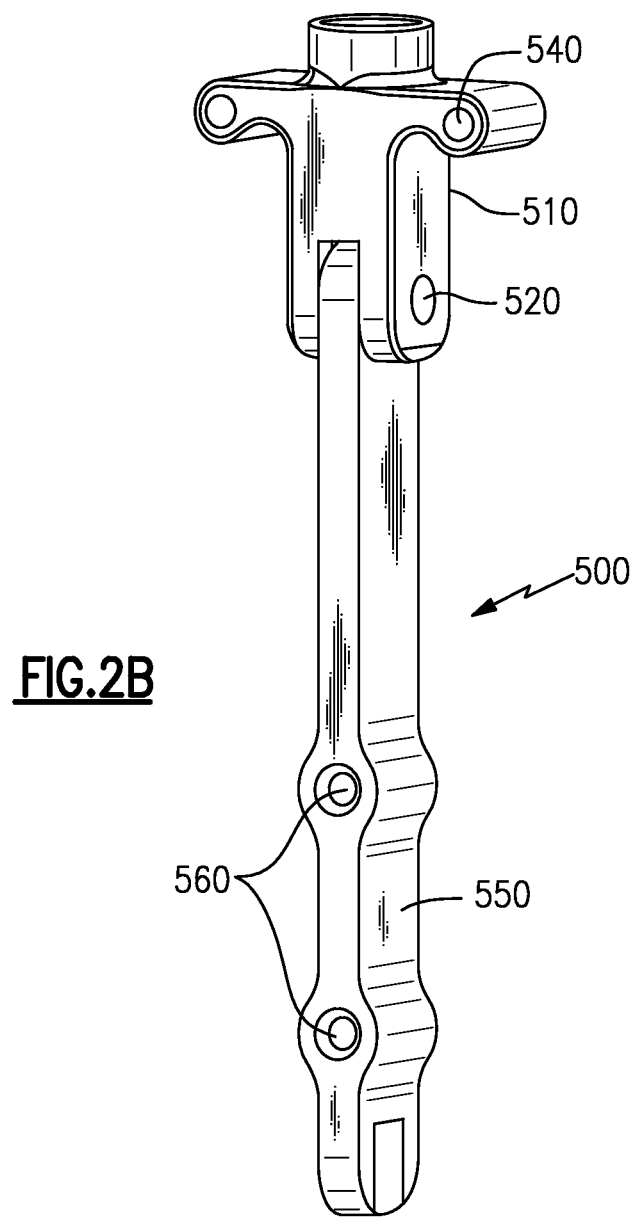
FIG. 2B illustrates another example linkage guide.

Another example femoral-tibial linkage guide 500 that can be used in place of the femoral-tibial linkage guide 400 is illustrated in FIG. 2B. The femoral-tibial linkage guide 500 includes a yoke 510 and a pin drill guide 550. The yoke 510 includes pin holes 540 that receive guide pins placed in the femoral bone. The pin drill guide 550 is secured to the yoke 510 with a pin 520 and is rotatable about the pin 520. The pin drill guide 550 also includes one or more pin holes 560 for the alignment and placement of the guide pins in the tibia. In the illustrated embodiment, the pin drill guide 550 includes two pin holes 560.

FIG. 2C illustrates yet another example femoral-tibial linkage guide 501 that can be used in place of the femoral-tibial linkage guide 400 illustrated by FIG. 2A or the femoral-tibial linkage guide 500 illustrated by FIG. 2B. In this example, the femoral-tibial linkage guide 501 embodies a two-piece design that includes a yoke 503 and a linkage bar 505. The yoke 503 includes pin holes 507 that can receive guide pins (not shown) placed in the femoral bone. A tongue portion 509 of the linkage bar 505 can be received in a groove 511 of the yoke 503. The groove 511 may extend between a pair of leg extensions 513 of the yoke 503. In other words, it is not necessary for the linkage bar 505 to be fixedly secured to the yoke 503. The linkage bar 505 can also include one or more pin holes 515 for the alignment and placement of the guide pins in the tibia. In the illustrated embodiment, the linkage bar 505 includes three pin holes 515.

Figure 2D:
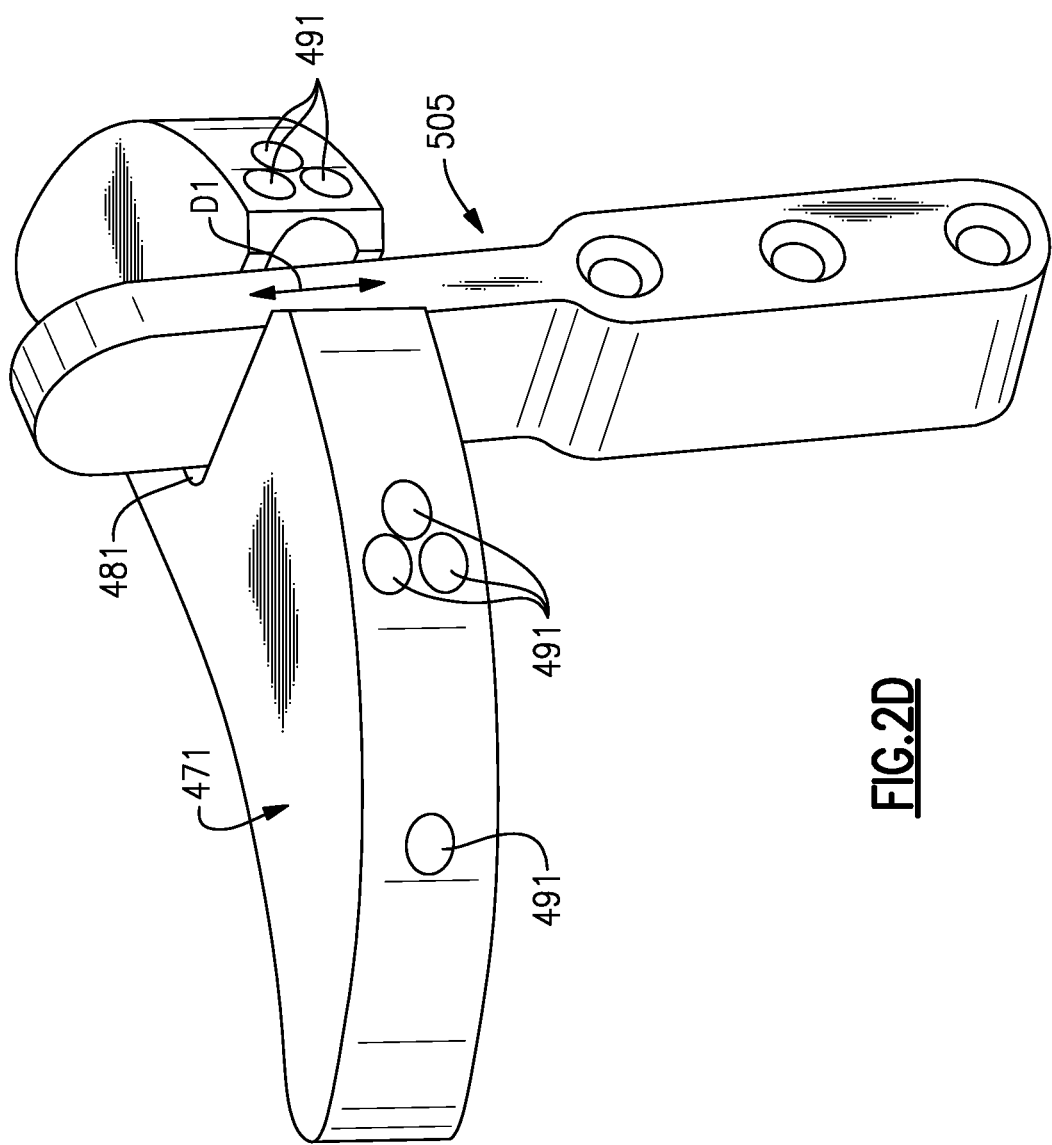
FIG. 2D illustrates an example cutting block.

As shown in FIG. 2D, an alternative cutting block 471 can be used with the linkage bar 505 of the femoral-tibial linkage guide 501. The cutting block 471 and the linkage bar 505 can be oriented and positioned relative to one another to prepare to make cuts in a second bone, such as tibial cuts in the tibia.

The exemplary cutting block 471 includes a slot 481 that is sized to accommodate at least a portion of the linkage bar 505. The cutting block 471 can be moved in a proximal-distal direction D1 along the linkage bar 505. The cutting block 471 can also be adjusted in the anterior/posterior direction by tilting the cutting block 471 on the linkage bar 505 while maintaining a position parallel to the bone in the varus-valgus direction. Once the cutting block 471 is located at a desired position, tibial guide pins (not shown) can be placed through one or more pin holes 491 on each side of the slot 481 in the cutting block 471. An additional pin hole 491 can also extend through the cutting block 471 to provide additional placement options.

Figure 2E:
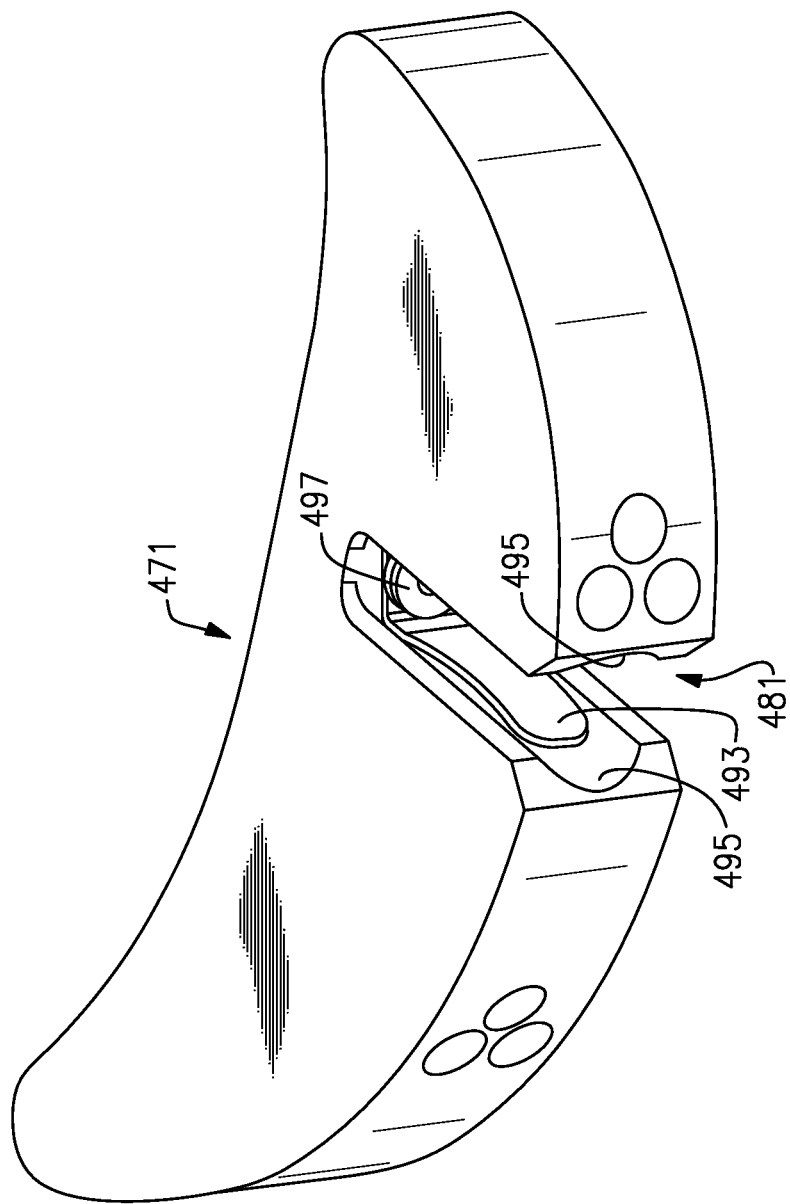
FIG. 2E illustrates additional features of the cutting block of FIG. 2D.

FIG. 2E illustrates additional features that may be incorporated into the cutting block 471. A spring 493 can be mounted within the slot 481. In one example, the spring 493 is a leaf spring, although other springs are contemplated as within the scope of this disclosure. A recess 495 is formed about the inner periphery of the slot 481. One or more springs 493 can be mounted within the recess 495, such as with a fastener 497. The spring(s) 493 acts to removably retain the linkage bar 505 within the slot 481 of the cutting block 471 during use (see FIGS. 2D and 2F).

Figure 2F:
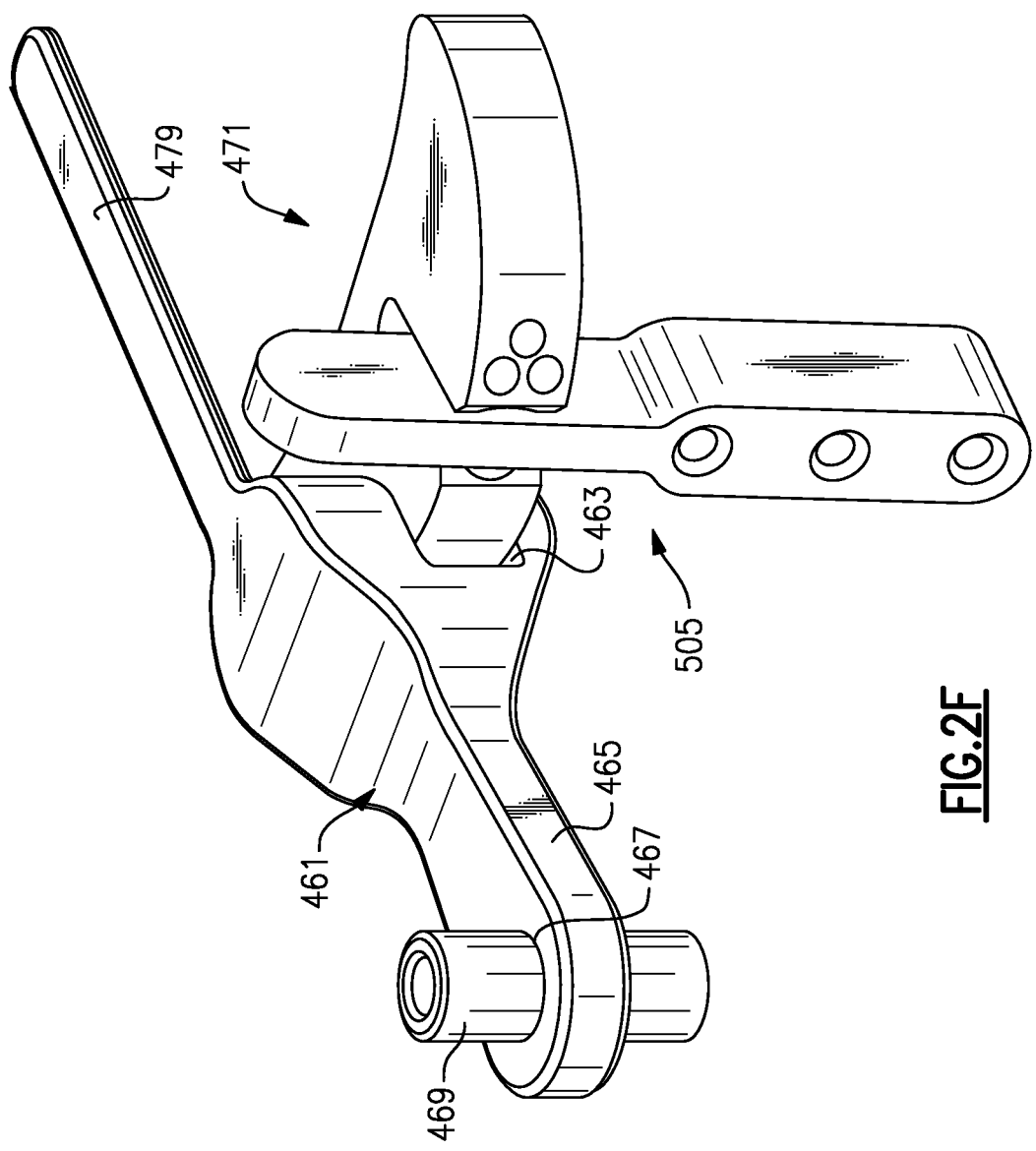
FIG. 2F illustrates an example slope indicator.

As shown in FIG. 2F, an optional slope indicator 461 can be used with the cutting block 471 and the linkage bar 505 to visually check the anterior/posterior slope alignment and can also be used to set a depth of a bone cut (such as approximately 8 mm distal of the tibial plateau, in one example). The slope indicator 461 has a slot 463 that can be sized to be received around the cutting block 471. An arm 465 extends from the slope indicator 461 and includes a through hole 467 that is sized to receive an alignment rod 469 which allows a user to visualize the anterior/posterior slope and perform any necessary adjustments to the positioning of the cutting block 471 prior to making any cuts. A second arm 479 extends in an opposite direction from the arm 465 and may rest against the tibial plateau to provide for additional visualization and adjustment of the anterior/posterior slope.

Figure 3A:
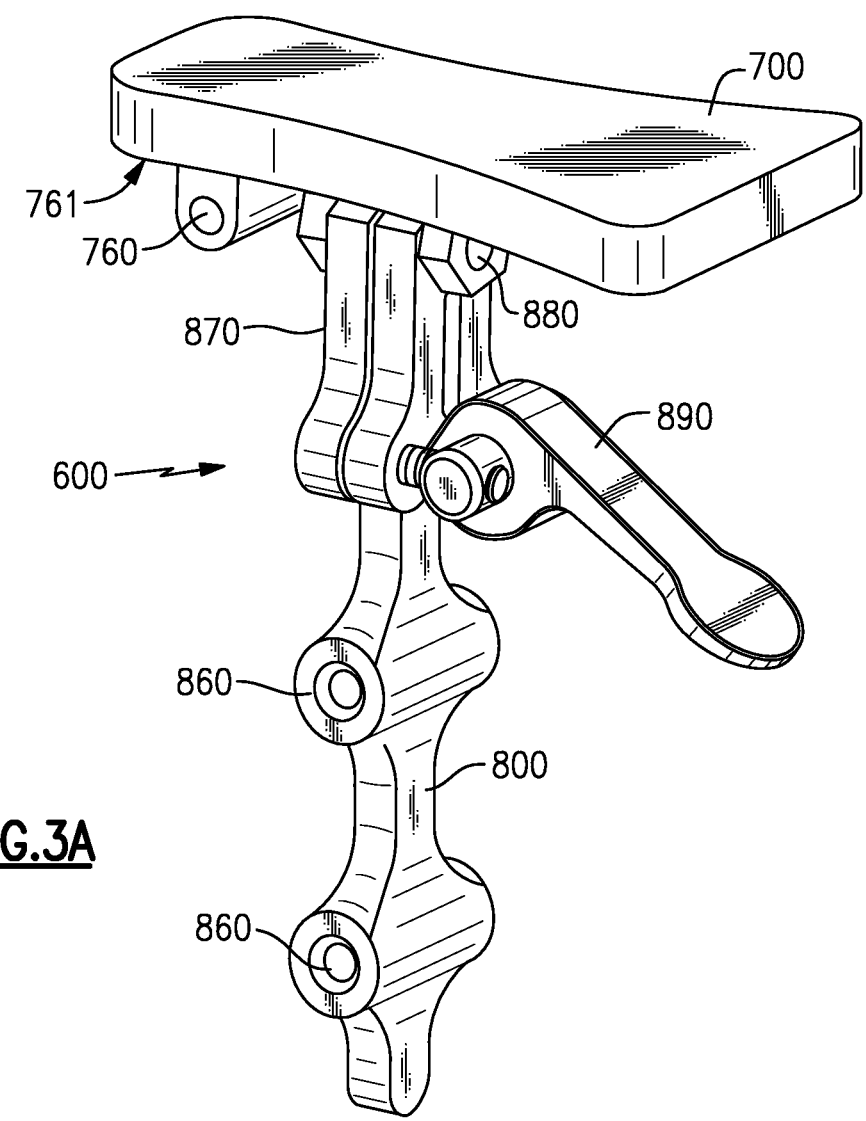
FIG. 3A illustrates a tibial cutting block assembly for use with the linkage guide of FIG. 2B.

FIG. 3A illustrates a tibial cutting block assembly 600 that can be used in combination with the guide assembly 101 and the femoral-tibial linkage guide 500. The tibial cutting block assembly 600 includes a cutting block 700 and a tibial alignment guide 800. The tibial alignment guide 800 includes one or more pin holes 860 for receiving a guide pin that is placed in the tibia. The tibial alignment guide 800 can also include an adjustment mechanism 870 that can be adjusted to lengthen or shorten the tibial alignment guide 800 as required based on a patient's anatomy.

The cutting block 700 is attached to the tibial alignment guide 800 via a pin 880. The pin 880 permits the cutting block 700 to rotate in the anterior/posterior plane and allows the surgeon to adjust the anterior/posterior slope based on the patient's anatomy. A locking lever 890 tightens and substantially locks the tibial cutting block assembly 600 once the final adjustments for length and slope are made. The cutting block 700 can also include a through hole 760 that extends from its bottom surface 761 for placement of a guide pin to provide additional security to the assembly prior to cutting.

Figure 3B:
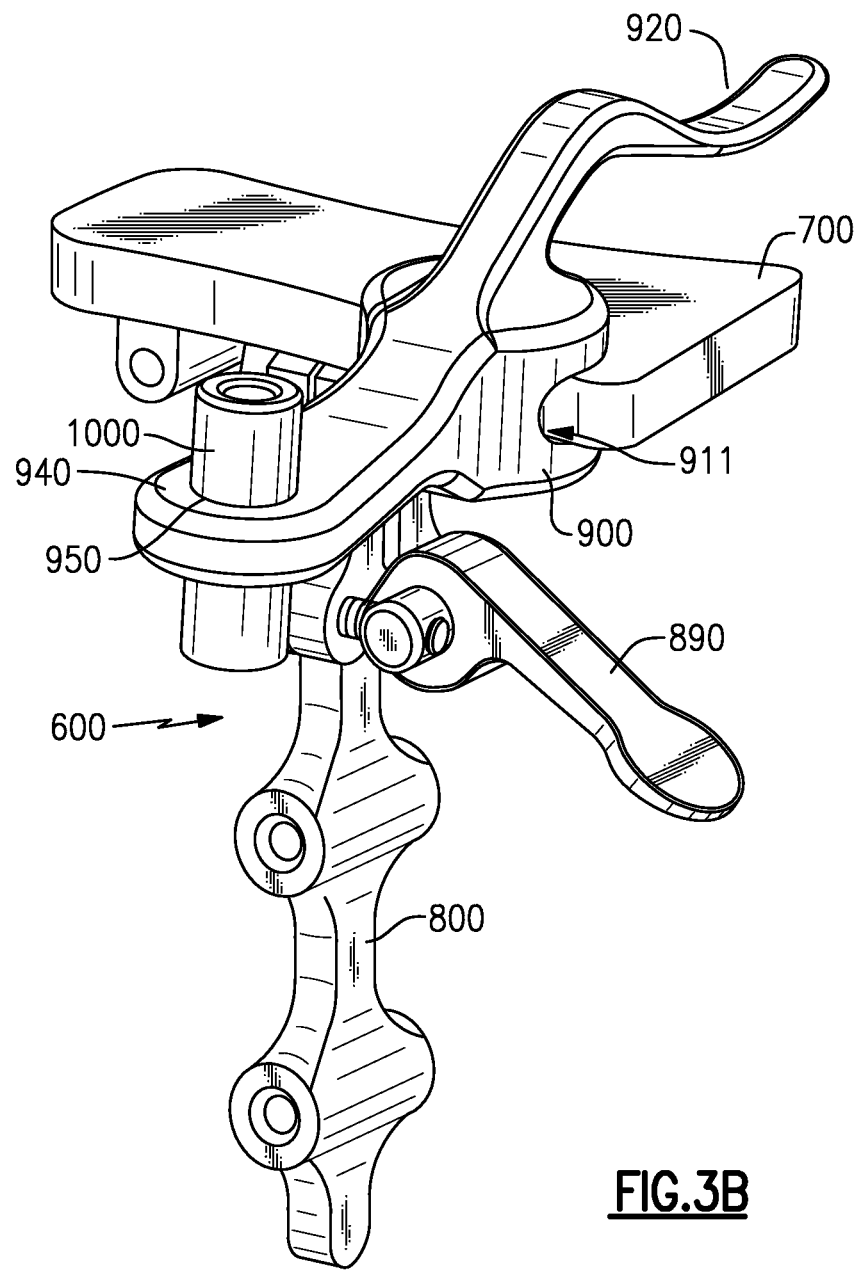
FIG. 3B illustrates an optional alignment clamp and rod for use with the tibial cutting block assembly of FIG. 3A.

Optionally, as illustrated in FIG. 3B, a tibial stylus 900 can be used with the tibial cutting block assembly 600 to provide the surgeon with an additional frame of reference for determining the proper placement of the tibial cutting block assembly 600. The tibial stylus 900 attaches to the cutting block 700, such as via opening 911. An arm 920 extends from the tibial stylus 900 for placement against the tibial plateau. The arm 920 is contoured to fit within the lowest level of the tibial plateau to provide a frame of reference for the anterior/posterior slope. Also extending from the tibial stylus 900 is a bar 940 having a hole 950 that is sized to receive an alignment rod 1000 for visualization of the anterior/posterior slope.

Figure 4A:
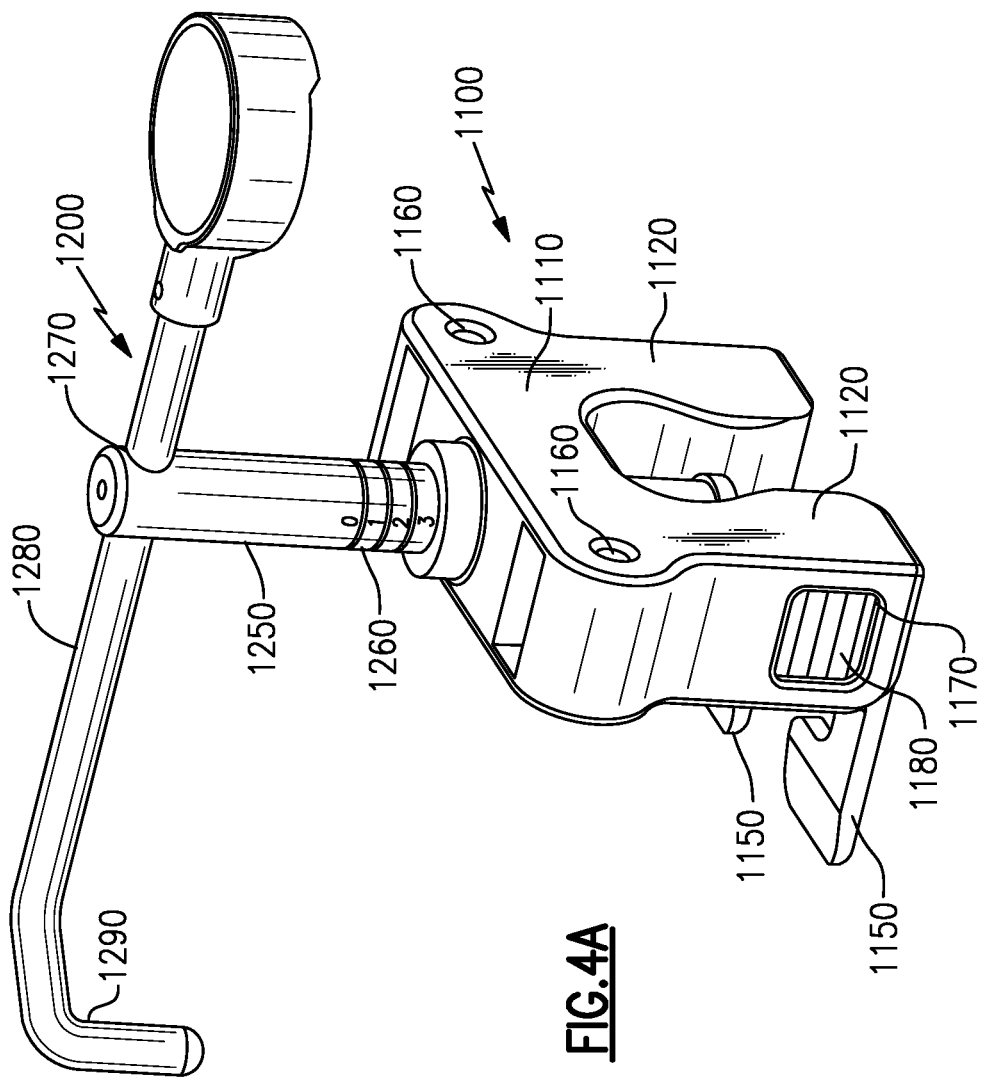
FIGS. 4A and 4B illustrate example alignment guide and sizing instrument assemblies for marking a position of an anterior, posterior and chamfer cut of a bone.
Figure 4B:
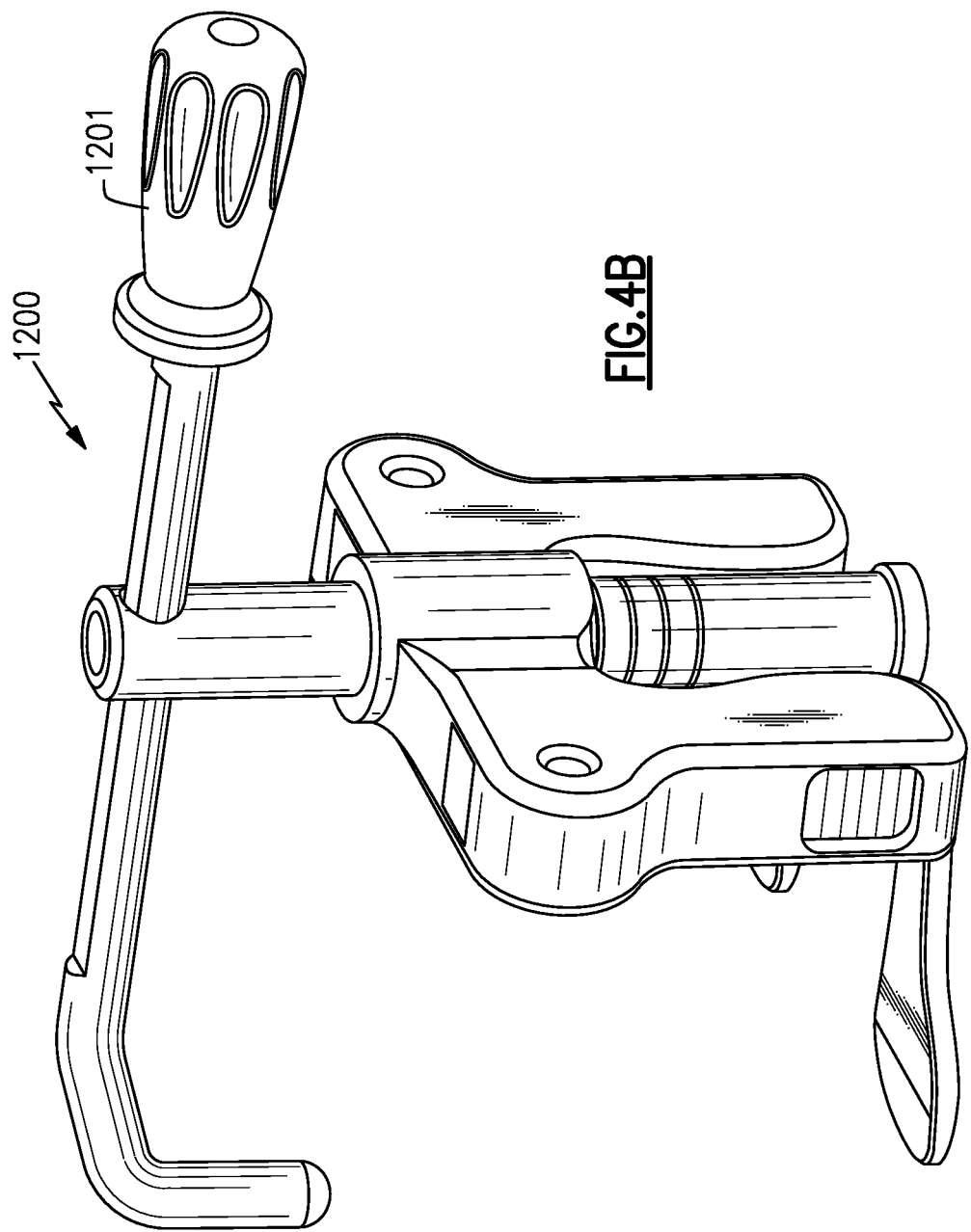

The total knee instrument set further includes an alignment guide 1100, as is illustrated in FIG. 4A. The alignment guide 1100 can be a femoral A/P alignment guide 1100 that accurately orients and positions the pins of a cutting block 1500 (See FIG. 5) to prepare the cutting block 1500 for making anterior, posterior and chamfer cuts in a bone, such as the femur. The femoral A/P alignment guide 1100 establishes a U-shape with a base 1110 and arms 1120 extending from each side of the base 1110. The base 1110 includes pin holes 1160 that can receive femoral guide pins. Extending from each arm 1120 is a foot 1150 for placement against the femoral condyle. The feet 1150 are adjustable to account for any internal or external rotation of the patient's knee (i.e., shifting of femur about the condyles to create either a pigeon toed or duck footed configuration). A visualization window 1170 is located on one or both arms 1120 and reveals a measurement scale 1180. The measurement scale(s) 1180 can be set to a depth that corresponds to an amount of the diseased cartilage of the patient. The amount of diseased cartilage is measured prior to adjustment of the feet 1150 of the femoral A/P alignment guide 1100, as is further discussed below. In this way, the cuts ultimately made to the bone are customized to a particular patient based on an amount of diseased cartilage that is measured and based on the patient's original anatomy pre-disease.

The femoral A/P alignment guide 1100 can further include a sizing template 1200 that extends from the base 1110. The sizing template 1200 includes a sliding rod 1250 and a curved arm 1280 that are used to determine the size of the femoral implant to be surgically implanted. For example, the sizing template 1200 can be used to determine the size of the total knee implant that will ultimately be implanted into a patient. The sliding rod 1250 is slidingly received by the base 1110. Markings 1260 of the sliding rod 1250 correlate to the size of the femoral implant to be used. A distal end of the sliding rod 1250 includes a hole 1270 for receiving the curved arm 1280 of the sizing template 1200. The curved arm 1280 can include a hook 1290 that rests against the femur to determine the size of the femoral implant to be used. The sizing template 1200 can optionally include a handle 1201 (see FIG. 4B).

Figure 5:
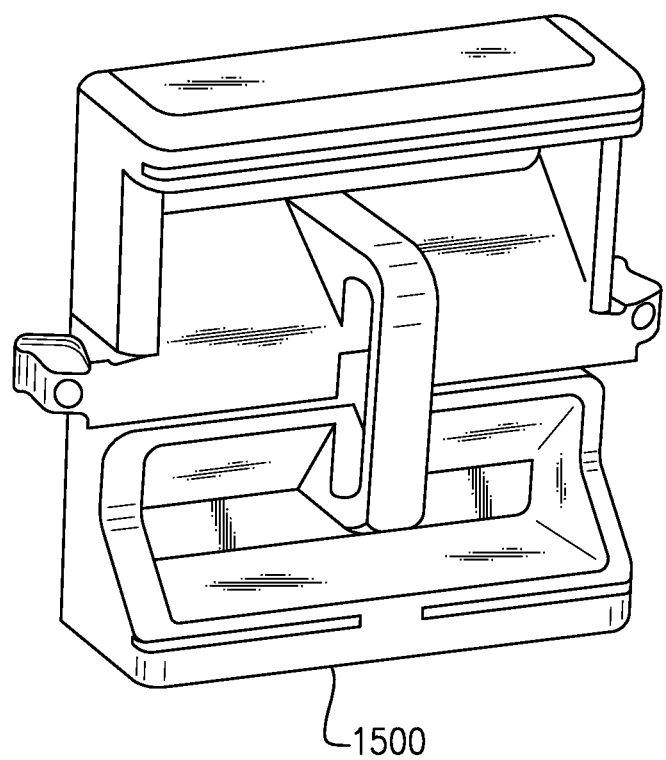
FIG. 5 illustrates a cutting block for the anterior, posterior and chamfer cuts of a bone.

A cutting block 1500 is illustrated by FIG. 5. The cutting block 1500 can be used to orient and position the anterior, posterior and chamfer cuts based on the placement of the femoral A/P alignment guide 1100, as is further discussed below. In one example, the cutting block 1500 is a 4-in-1 cutting block that can be used to orient and position anterior, posterior and chamfer cuts.

An example method of using the total joint instrument set illustrated by FIGS. 1-5 to prepare a patient for a total knee implant is described below. The unique instrumentation allows a surgeon to mechanically link the femoral cut to the tibial cut to ensure that these cuts are made in parallel. The surgeon is also able to independently adjust the femoral cuts being made in the varus and valgus directions and internal and external rotation based on a previous measurement of a patient's diseased cartilage. The femoral alignment can be performed extramedullary without having to insert the alignment portion into the medullary canal of the femur.

Figure 6:
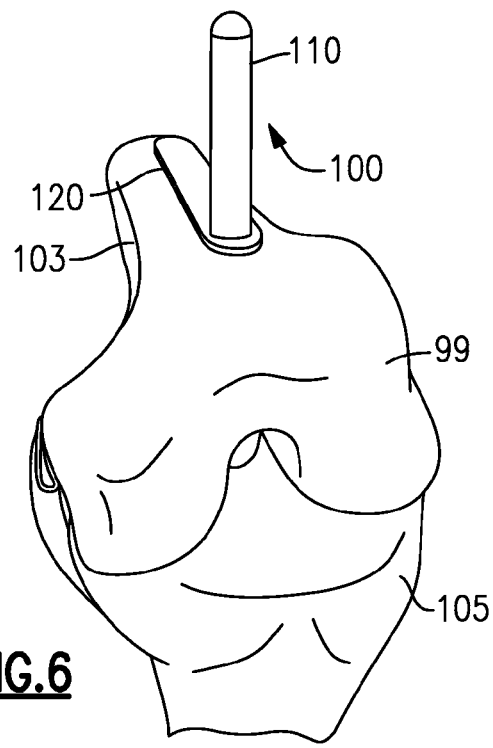

As illustrated by FIG. 6, the method begins by placing the extramedullary femoral alignment guide 100 of the guide assembly 101 against a patient's femur 99 so that the alignment bar 120 is in alignment with a femoral shaft 103 of the femur 99. This is a relatively non-invasive step as compared to alignment instrumentation that requires reaming the femoral canal to position an alignment rod.

Figure 7:
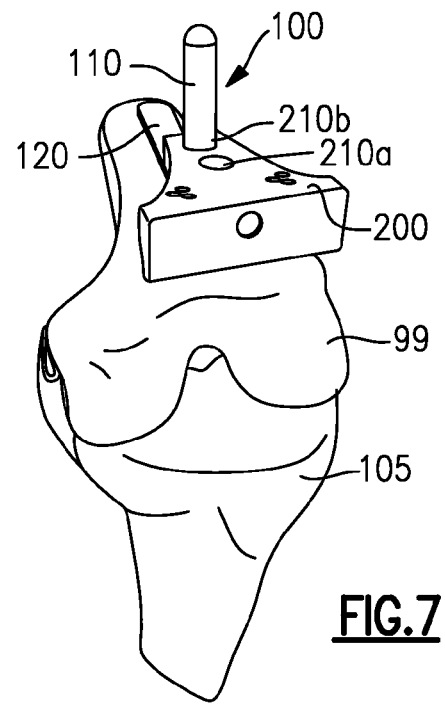

Once the extramedullary femoral alignment guide 100 is positioned, the femoral cutting block 200 is placed over the connecting rod 110, as shown in FIG. 7. The connecting rod 110 is inserted through one of the holes 210a, 210b, depending upon a desired positioning of the extramedullary femoral alignment guide 100 and the femoral cutting block 200.

Figure 8A:
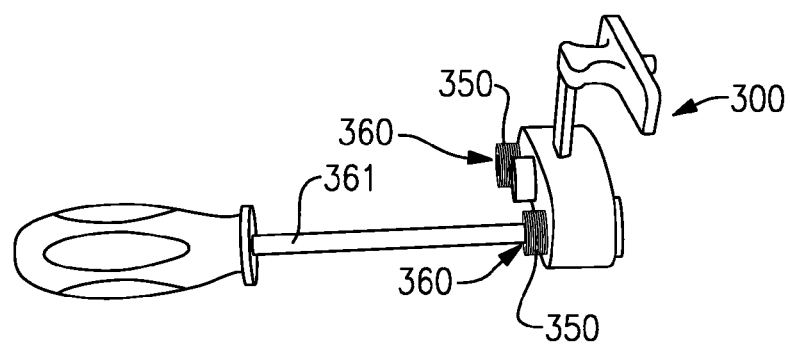

Referring to FIGS. 8A-8D, each cylinder 350 of the adjustable femoral varus/valgus alignment guide 300 can be adjusted by engaging the driver engagement features 360 with a tool 361. The actual position of each cylinder 350 is based on the depth of the diseased cartilage (previously determined, such as by measuring a healthy condyle on the same or opposite knee). In other words, the depth of the femoral cut is based on the depth setting of the cylinders 350. The adjustable femoral varus/valgus alignment guide 300 is connected to the cutting surface 250 of the femoral cutting block 200 (FIG. 8D). In one example, the surfaces are magnetically connected. The guide portion 340 can slide along connecting element 320 until the cylinders 350 are aligned with the apex of the femoral condyles or until a desired positioning as determined by a surgeon is otherwise reached.

Figure 9A:
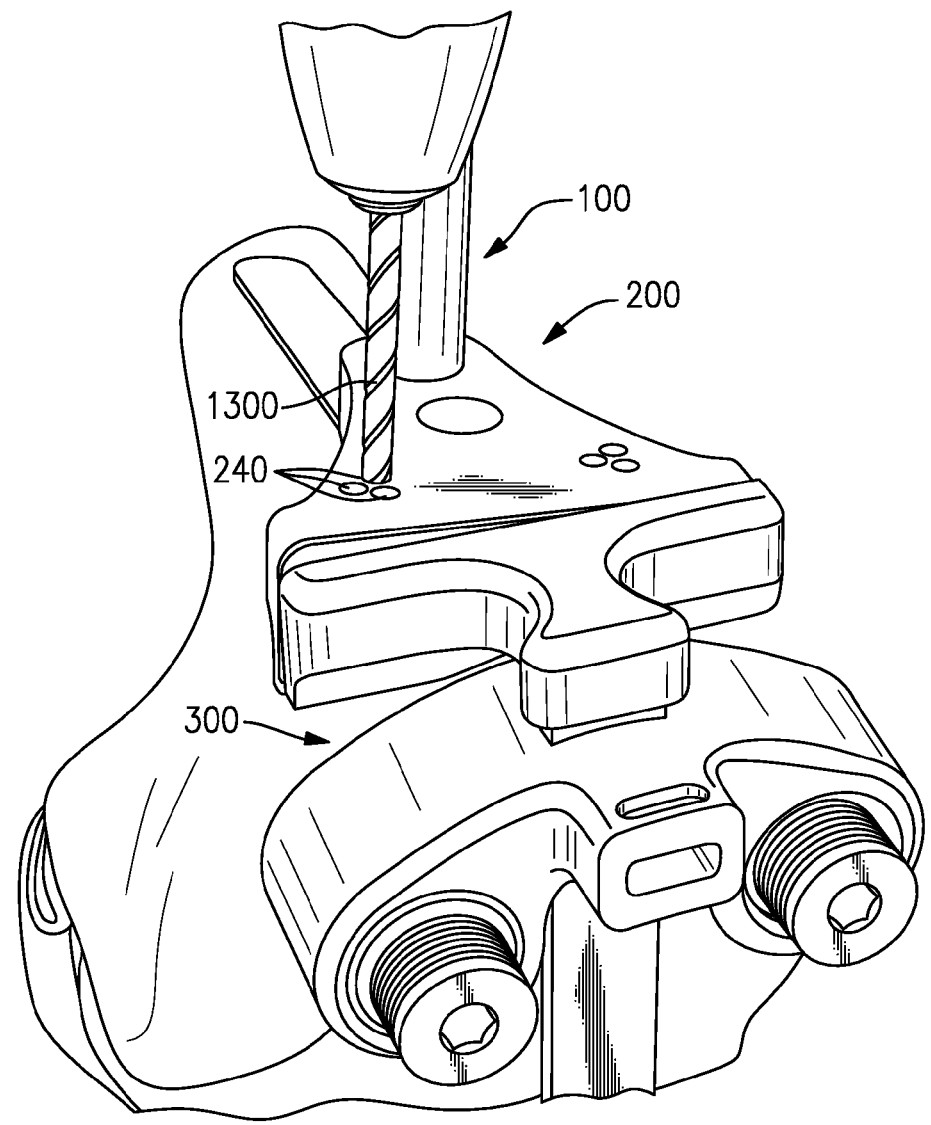
Figure 9B:
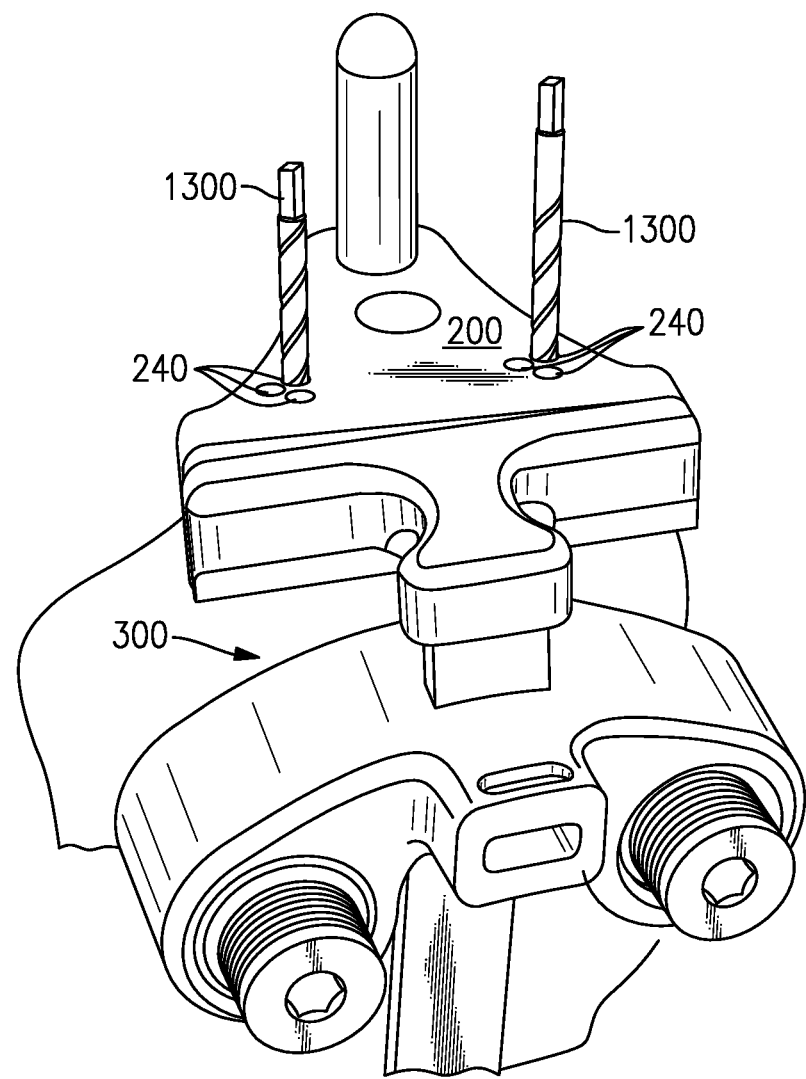
Figure 10:
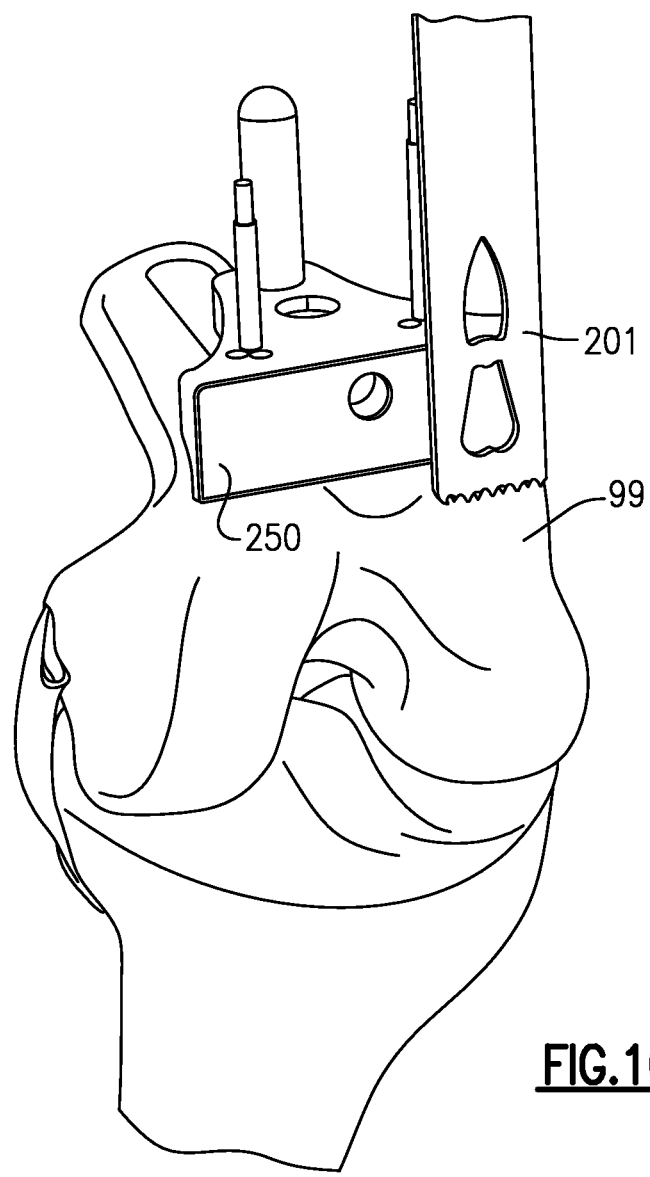
Figure 11:
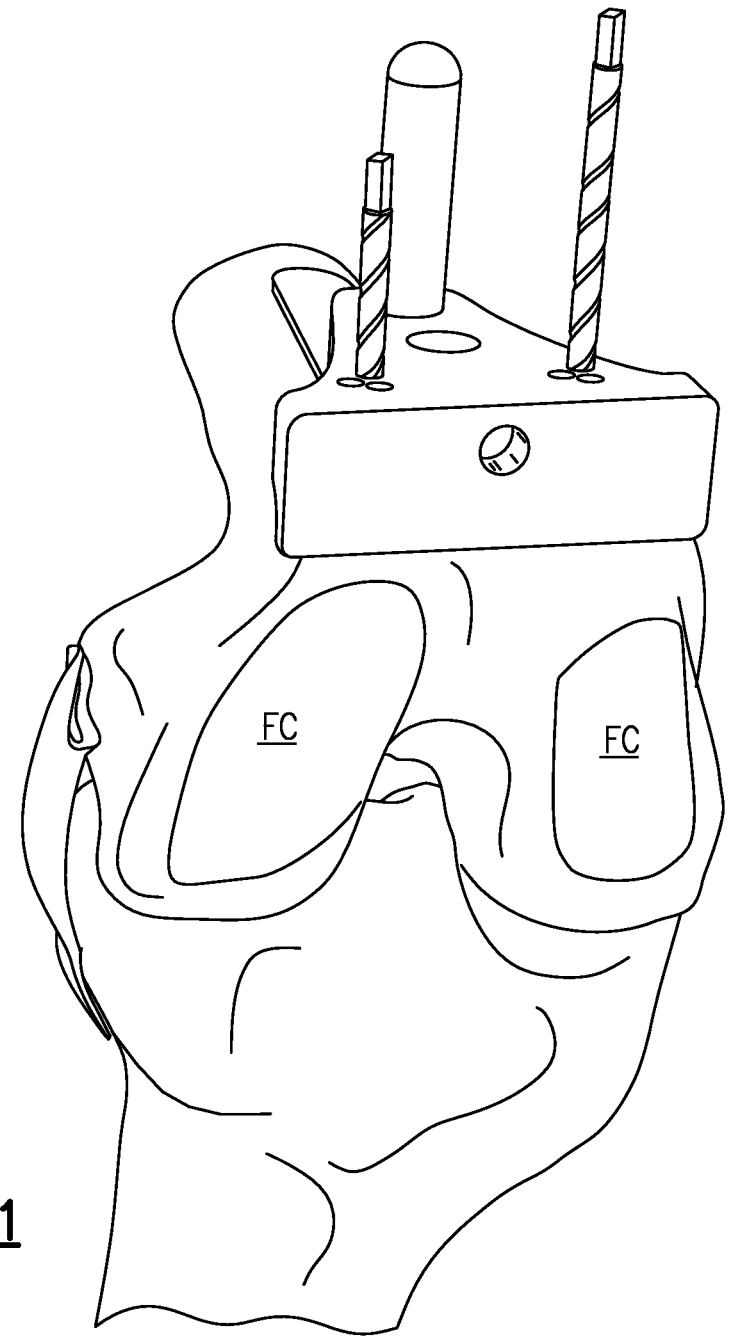

Once the adjustable femoral varus/valgus alignment guide 300 is set in the desired orientation and position, femoral guide pins 1300 are placed through at least two of the pin holes 240 on the femoral cutting block 200 as shown in FIGS. 9A-9B. Once the femoral guide pins 1300 have been properly positioned, the varus/valgus alignment guide 300 is disconnected from the femoral cutting block 200 and the femoral cuts FC are made with a cutting tool 201 as illustrated in FIGS. 10-11.

After the femoral cuts FC are made, the femoral cutting block 200 and the extramedullary femoral alignment guide 100 are removed, leaving only the femoral guide pins 1300 in place. The leg can then be extended so that it is straight.

Figure 12A:
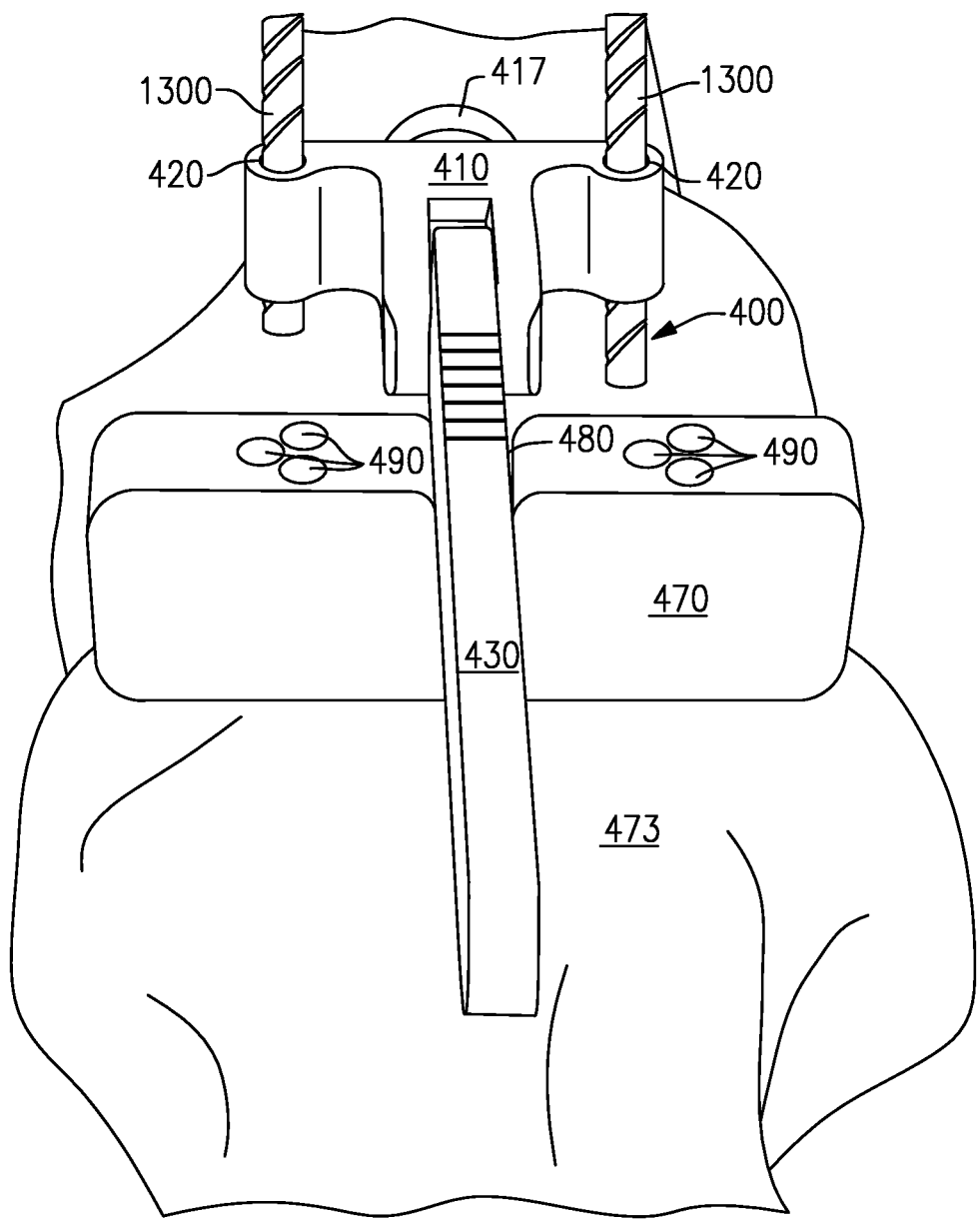
Figure 12B:
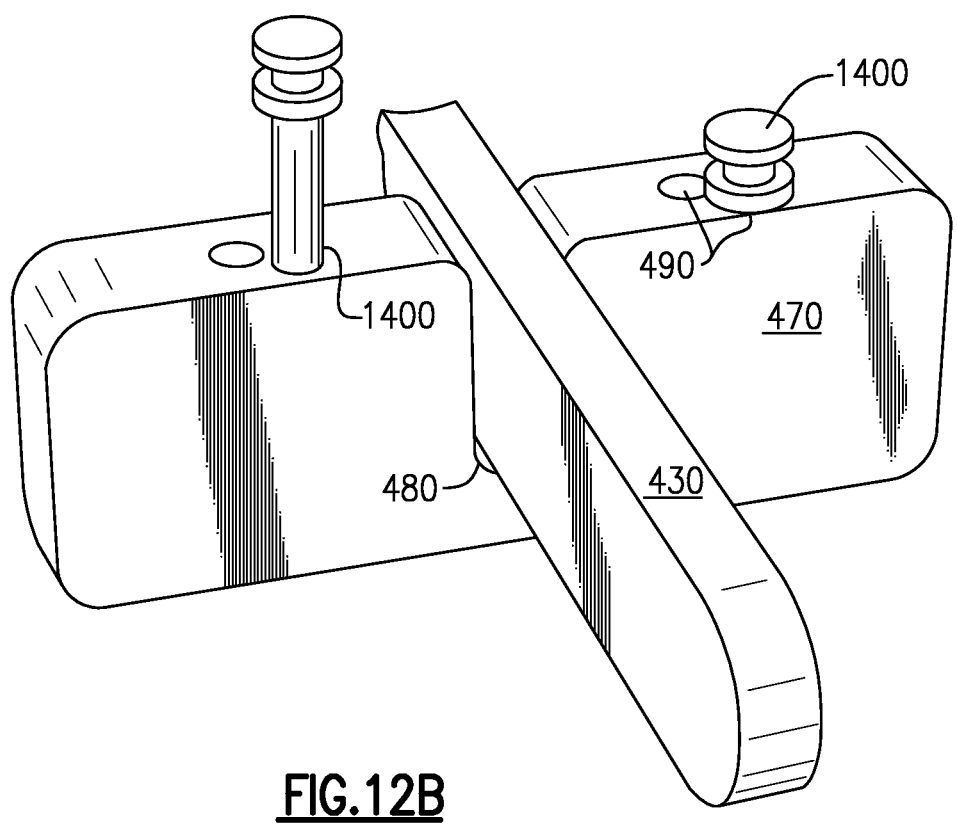
Figure 12C:
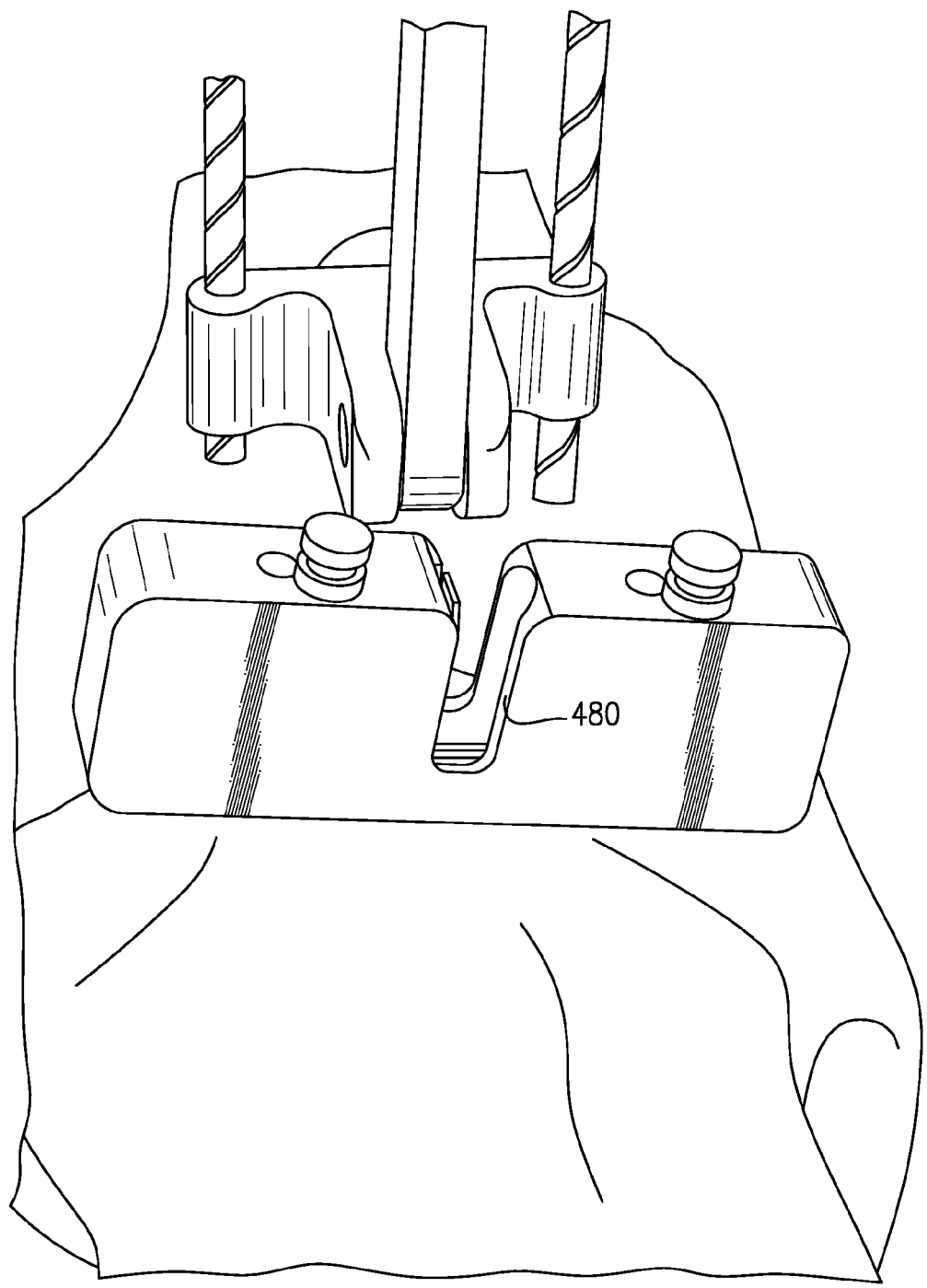

Referring to FIGS. 12A-12C, the femoral-tibial linkage guide 400 (or femoral-tibial linkage guide 500, as noted below) can be placed over the femoral guide pins 1300 through the pin holes 420 of the yoke 410 of the femoral-tibial linkage guide 400. In this way, the tibial cutting block 470 can be oriented and positioned parallel to the femoral cuts by mechanically linking a positioning of the femoral-tibial linkage guide 400 relative to a positioning of the guide assembly 101. That is, the tibial cuts and the femoral cuts can be made parallel to one another by mechanically linking the femoral-tibial linkage guide 400 and the guide assembly 101 by using the femoral guide pins 1300 of the guide assembly 101 to properly orient and position the femoral-tibial linkage guide 400 such that the tibial cutting block 470 is parallel to the femoral cuts. In this disclosure, the term "mechanically linking" describes that the orientation and positioning of a particular instrument is based at least in part on the orientation and positioning of another instrument.

The tibial alignment bar 430 and the tibial cutting block 470 extend along a tibial shaft 473 as shown in FIG. 12A. The position of the cut in the proximal distal plane and also the anterior/posterior slope can also be adjusted. For example, the tibial cutting block 470 can be moved along the tibial alignment bar 430 until a desired position of the cut in the proximal-distal direction is reached. Then, the tibial cutting block 470 can be tilted within the slot 480 to adjust for the desired anterior/posterior slope. As an additional check, the alignment clamp 450 (not shown) can be placed on the tibial cutting block 470 with the alignment rod 485 extending through the hole 455 of the alignment clamp 450. The surgeon can visualize the anterior/posterior slope from the alignment rod 485 and make any desired adjustments by tilting the tibial cutting block 470. Once the position is finalized, the locking screw 417 is tightened to secure the guide assembly. The tibial guide pins 1400 are then placed through the pin holes 490 on either side of slot 480 of the cutting block 470 (as shown in FIG. 12B). Once the tibial guide pins 1400 are positioned, the femoral-tibial linkage guide 400 and femoral guide pins 1300 are removed leaving the cutting block 470 in place (FIG. 12C). The tibial cut is then made against the cutting block, such as by using a cutting tool 201 similar to that shown in FIG. 10.

The femoral-tibial linkage guide 500 can alternatively be used instead of the femoral-tibial linkage guide 400. The femoral-tibial linkage guide 500 is placed over the femoral guide pins 1300 through the pin holes 540. The patient's leg is then extended to a straight position and the pin drill guide 550 of the femoral-tibial linkage guide 500 is placed against the tibia 105. Tibial guide pins 1400 are placed through the pin holes 560 of the femoral-tibial linkage guide 500 ensuring that the tibial guide pins 1400 are placed generally perpendicular to the femoral guide pins 1300. The femoral-tibial linkage guide 500 is removed, the knee is flexed, and the tibial cutting block assembly 600 is placed over the tibial guide pins through pin holes 860.

The surgeon can adjust the placement of the cutting block 700 of the tibial cutting block assembly 600 by lengthening or shortening the tibial alignment guide 800. Additional positioning can be accomplished in the anterior/posterior directions by tilting the cutting block 700 about the pin 880. The tibial stylus 900 can be positioned on the cutting block 700 to assist in determining the correct anterior/posterior slope. The arm 920 of tibial stylus 900 is placed in the lowest spot of the patient's tibial plateau. The alignment rod 1000 is placed through the hole 950 of the tibial stylus to provide the surgeon with visualization of the anterior/posterior slope. The surgeon can adjust the anterior/posterior slope by tilting the cutting block 700 to match the desired anterior/posterior slope. Once a positioning of the cutting block 700 is selected, the locking lever 890 is clamped down to secure the tibial cutting block assembly 600 in the desired positioning. The tibial stylus 900 is removed and a tibial cut is made against the cutting block 700. The tibial cutting block assembly 600 allows a surgeon to make adjustments for the anterior/posterior slope as well as proximal and distal adjustments while keeping the cut parallel in the varus-valgus direction (also known as the coronal plane).

Figure 13A:
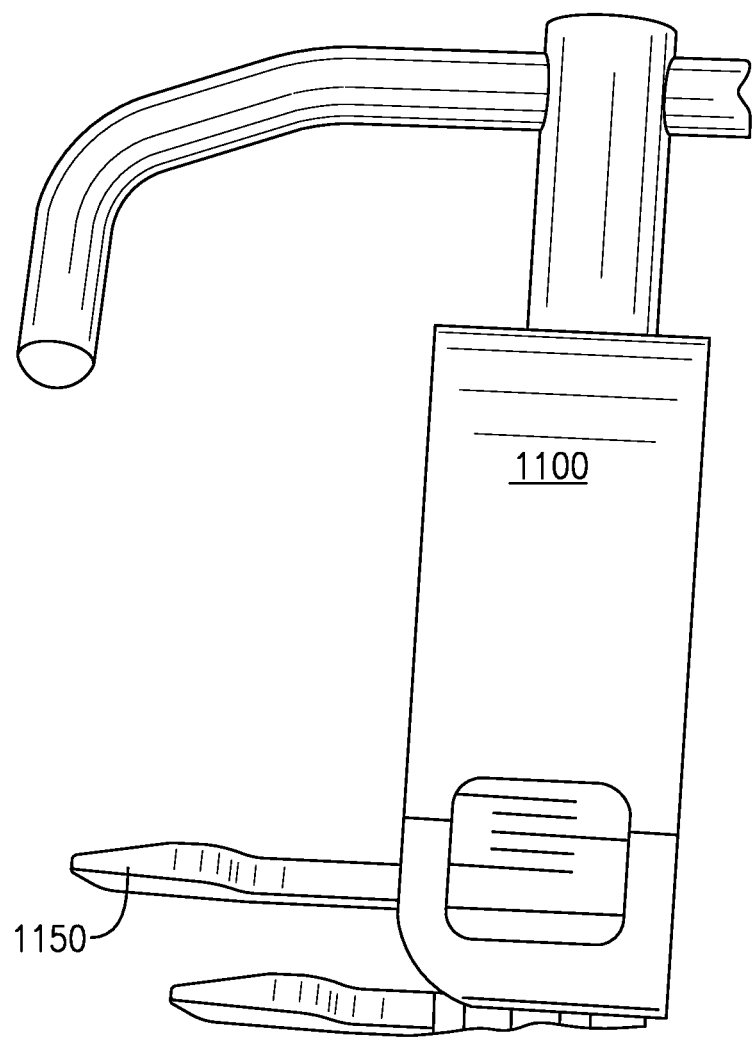
Figure 13B:
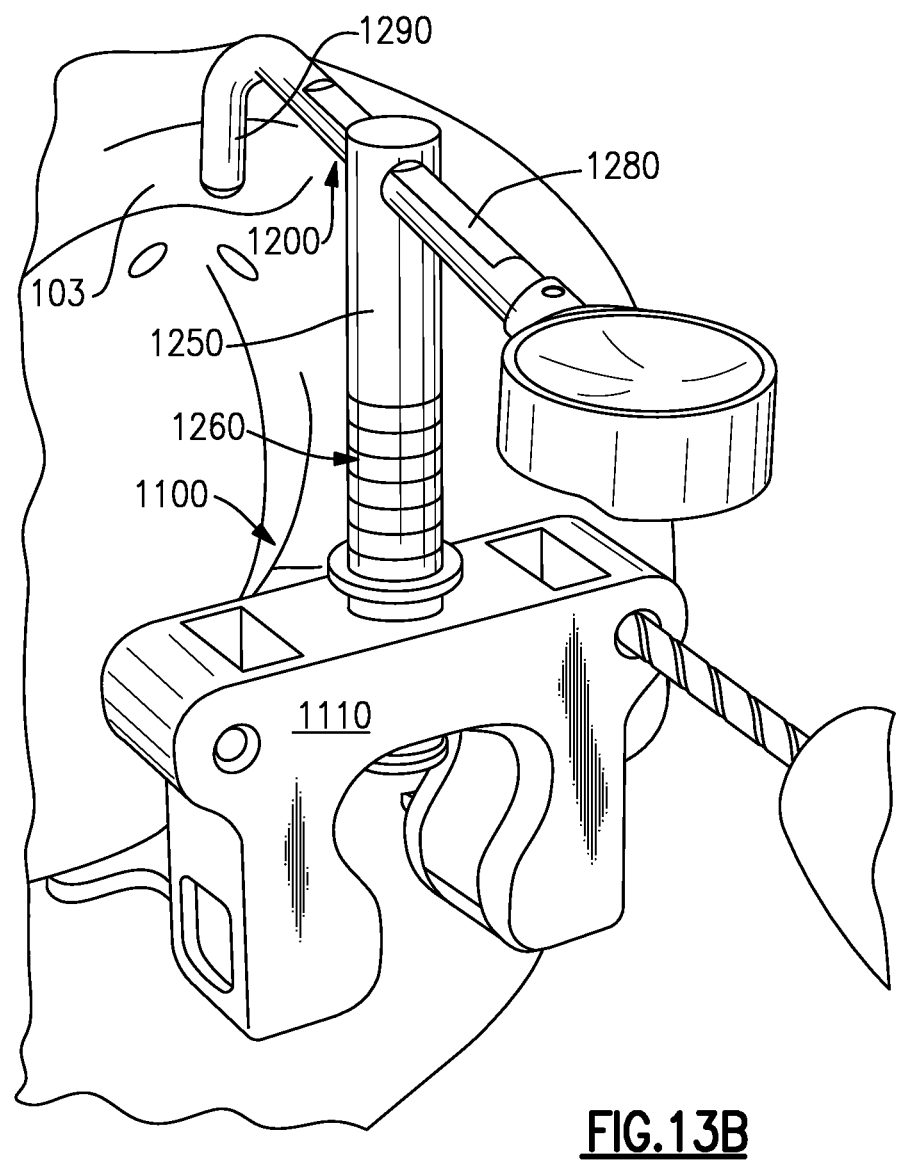
Figure 13C:
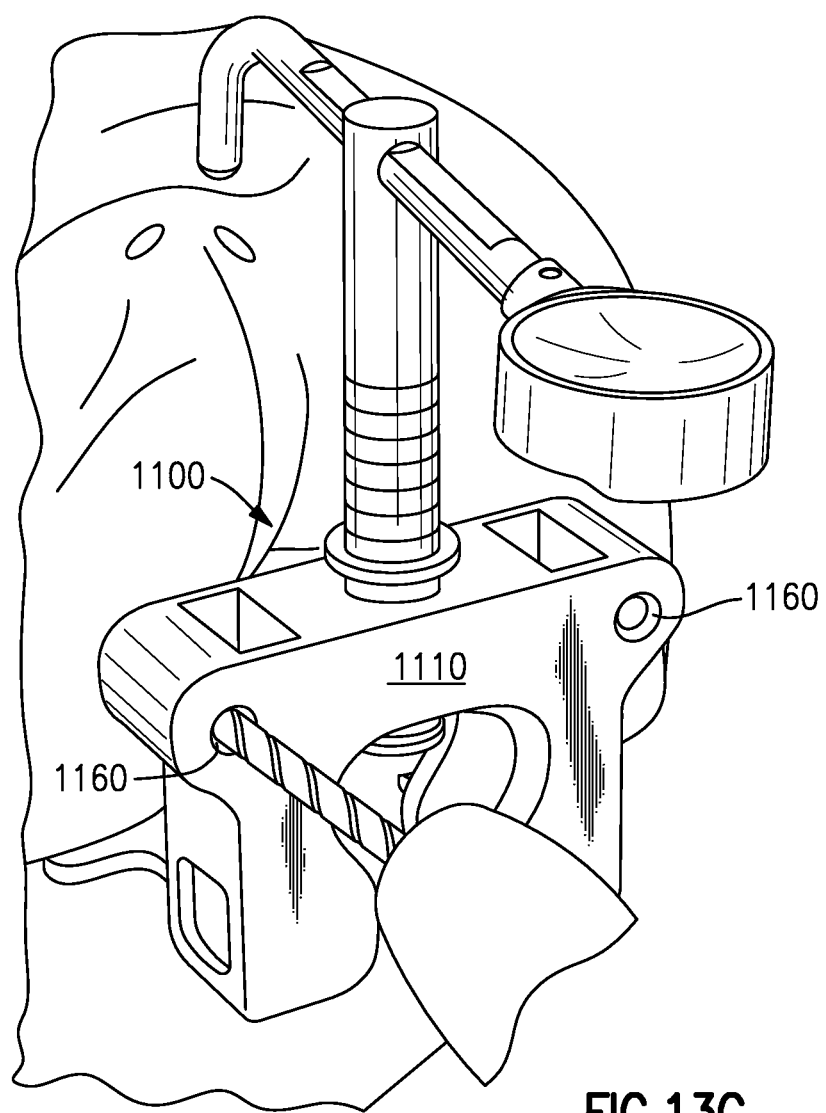

Referring to FIGS. 13A-13C, the femoral A/P alignment guide 1100, which sets the internal and external rotation of the implant and provides for sizing of the femoral implant, is used to orient and position the femoral anterior, posterior and chamfer cuts. The femoral A/P alignment guide 1100 allows the cuts to be made based on the depth of the diseased cartilage so that removal of healthy bone is minimalized. The femoral A/P alignment guide 1100 has individual feet 1150 that are adjustable to compensate for the depth of the diseased cartilage (See FIG. 13A).

Each foot 1150 is set at a depth that corresponds to an amount of the diseased cartilage in order to restore the patient to his/her original anatomy pre-disease after completion of the total knee implantation. The amount of diseased cartilage is determined by a surgeon. For example, the amount of diseased cartilage can be determined based on measurements from a CT scan, an X-ray, direct visualization and measurement by the surgeon, or other suitable technique.

The femoral A/P alignment guide 1100 is placed against the femoral condyles with the knee in the flexed position (FIG. 13B). The hook 1290 of the sizing template 1200 can be extended to contact the femoral shaft 103. Once in the desired position, the size of the femoral implant to be used is determined by reading the markings 1260 along the sizing rod 1250.

Figure 14:
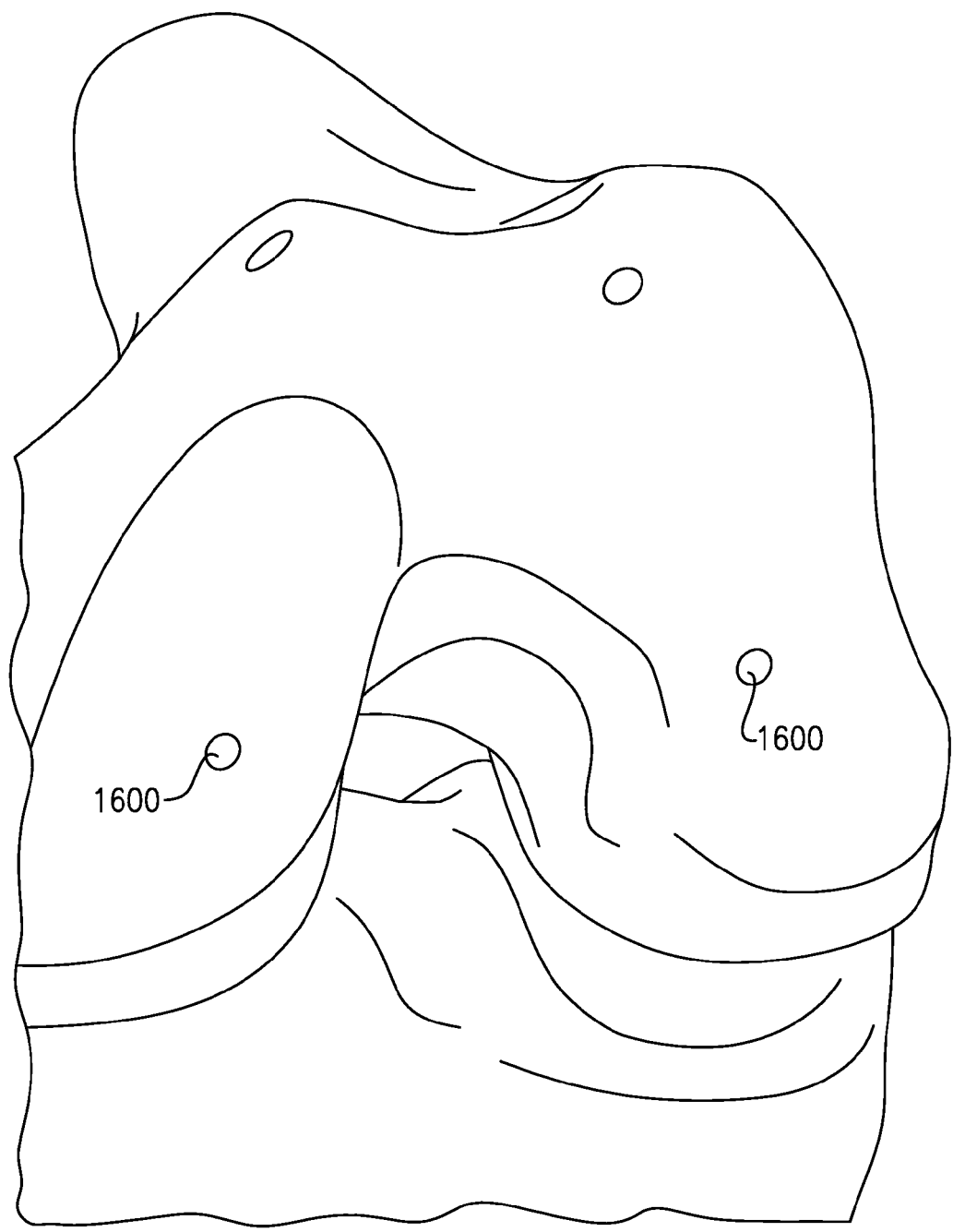
Figure 15A:
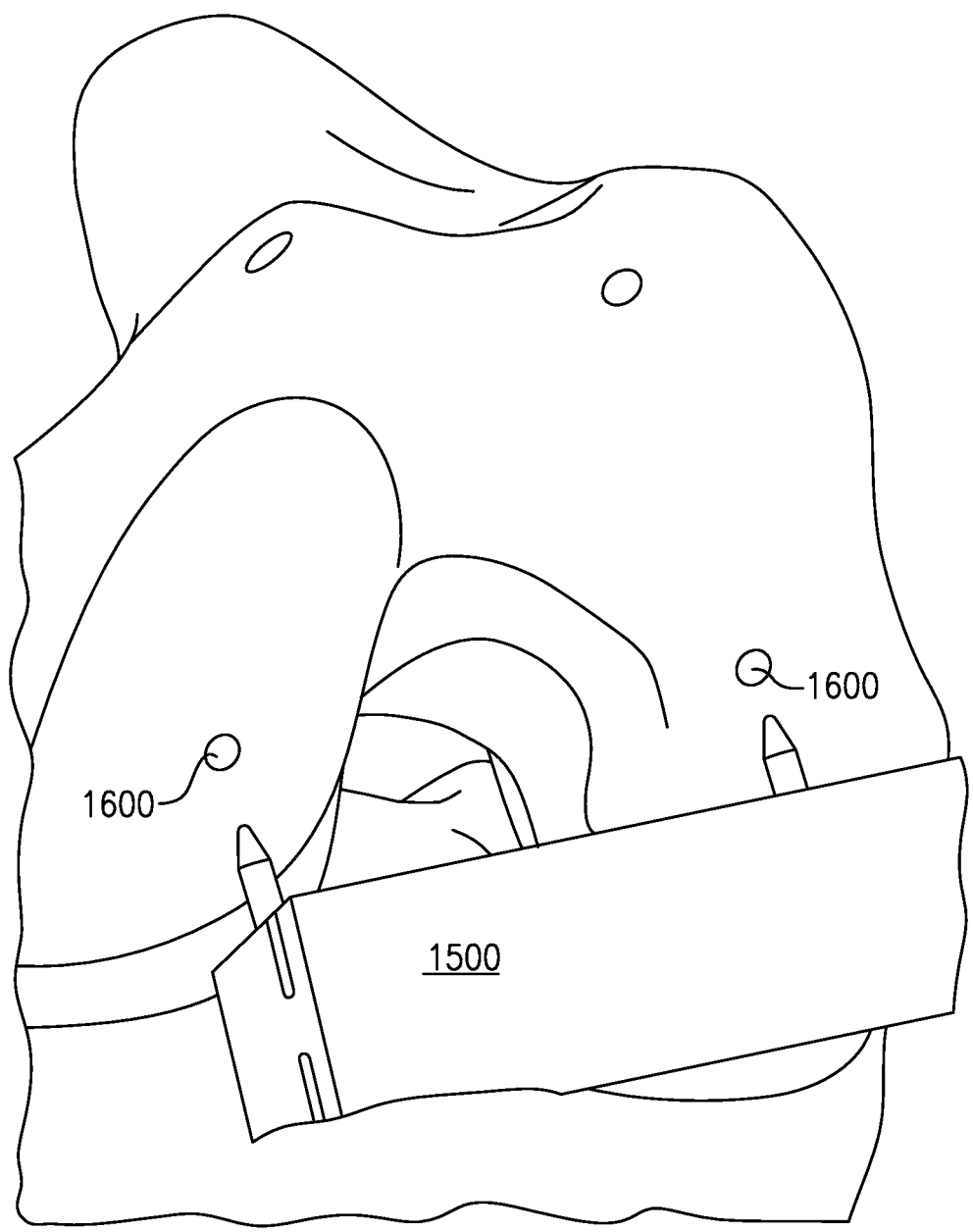
Figure 15B:
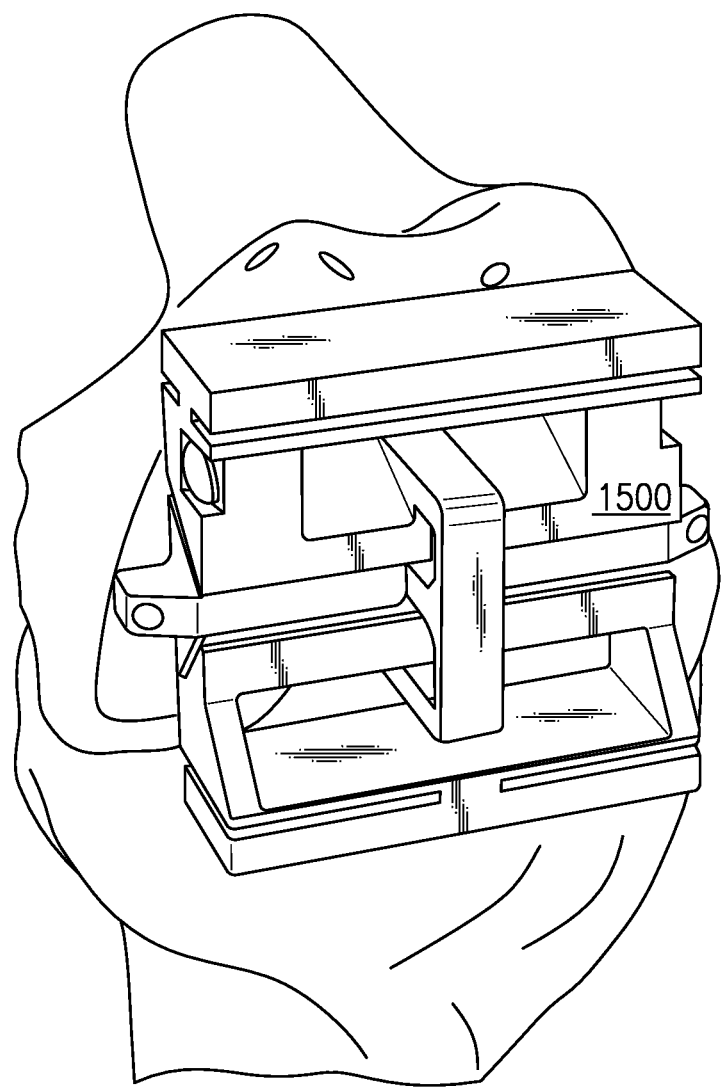

As shown in FIG. 13C and FIG. 14, the guide holes 1600 are next drilled through the pin holes 1160 of the base 1110 into the bone. The femoral A/P alignment guide 1100 is removed and the cutting block 1500 is placed in the guide holes 1600 as illustrated in FIGS. 15A-15B. The anterior, posterior and chamfer cuts can then be made using the cutting block 1500 and a cutting tool. Once all cuts are made, a total knee implant can be implanted.

Another example method of using the total joint instrument set illustrated in FIGS. 1-5 to prepare a patient's joint for a total joint implant is described below. The following method is similar to the method described above with respect to FIGS. 6-15 but may include slight modifications in the sequencing or instrumentation used and is therefore described as another embodiment. The unique instrumentation allows a surgeon to mechanically link a cut in a first bone (i.e., a femoral cut) to a cut in a second bone (i.e., a tibial cut) to ensure that these cuts are made in parallel. The surgeon is also able to independently adjust the femoral cuts being made in the varus and valgus directions and internal and external rotation based on a previous measurement of a patient's diseased cartilage. The femoral alignment can be performed extramedullary without having to insert the alignment portion into the medullary canal of the femur.

Figure 16:
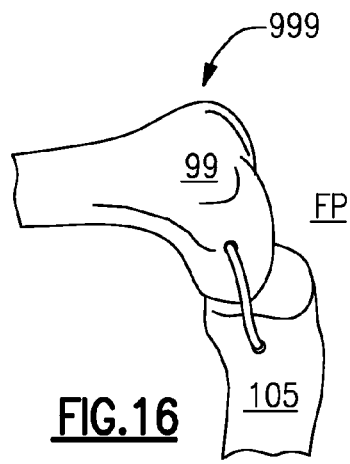
FIGS. 16, 17, 18, 19A, 19B, 19C, 19D, 20A, 20B, 21A, 21B, 21C, 22, 23, 24, 25, 26A, 26B, 26C, 27, 28A, 28B, 29, 30, 31, 32, 33A, 33B, 34A and 34B illustrate another example implementation of orthopedic surgical instrumentation for use in making various cuts in a patient's joint to prepare the patient for the implantation of a total joint implant.
Figure 17:
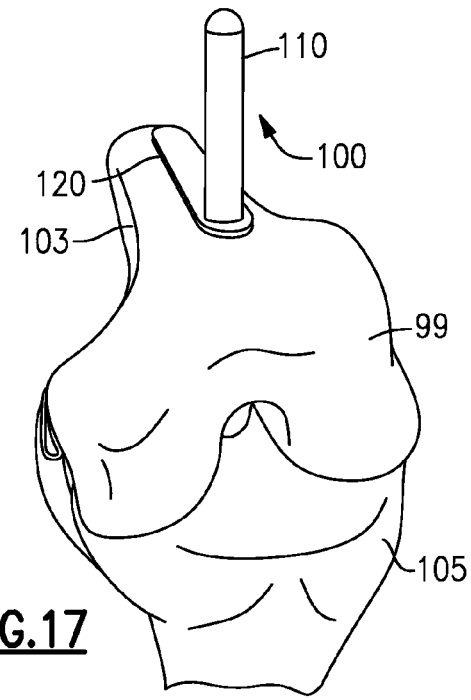

As schematically illustrated by FIG. 16, the method may begin by positioning a patient's knee 999 in a flexed position FP (i.e., the femur 99 is transverse to the tibia 105). As shown in FIG. 17, the extramedullary femoral alignment guide 100 of the guide assembly 101 (see FIG. 1A) can then be placed against a patient's femur 99 so that the alignment bar 120 is in alignment with a femoral shaft 103 of the femur 99. This is a relatively non-invasive step as compared to alignment instrumentation that requires reaming the femoral canal to position an alignment rod. In one embodiment, the alignment bar 120 can be positioned between the femoral shaft 103 and the soft tissue (not shown) of the patient.

Figure 18:
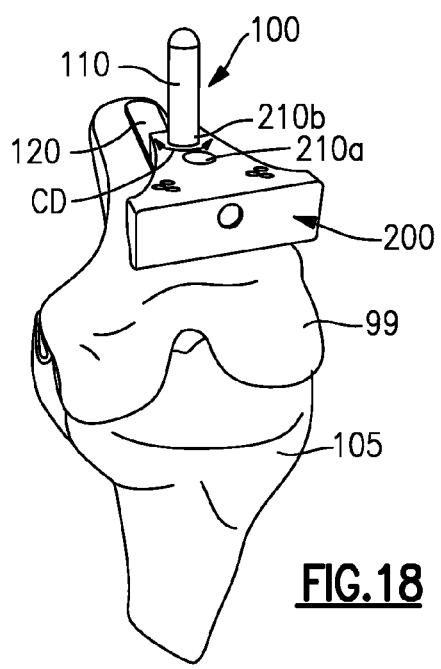

Once the extramedullary femoral alignment guide 100 is positioned, the femoral cutting block 200 can be placed over the connecting rod 110 as shown in FIG. 18. The connecting rod 110 is inserted through one of the holes 210a, 210b of the femoral cutting block 200, depending upon a desired positioning of the extramedullary femoral alignment guide 100 and the femoral cutting block 200. The femoral cutting block 200 can be rotated in a circumferential direction CD about the connecting rod 110 to achieve a desired positioning relative to the femur 99.

Figure 19A:
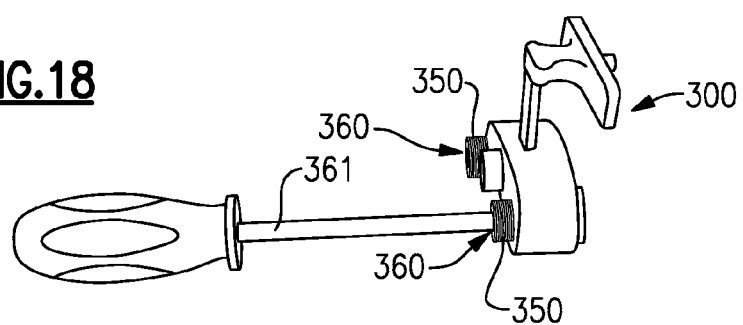
Figure 19B:
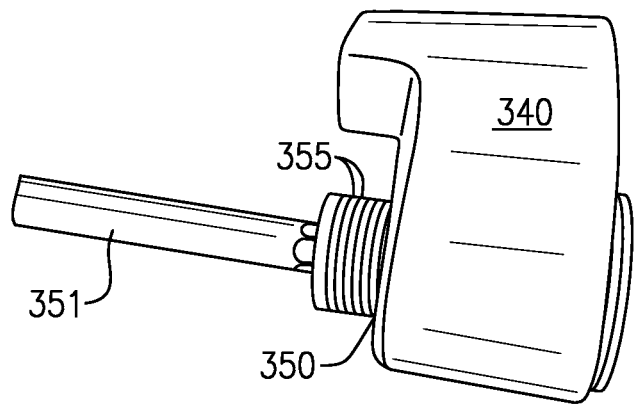
Figure 19C:
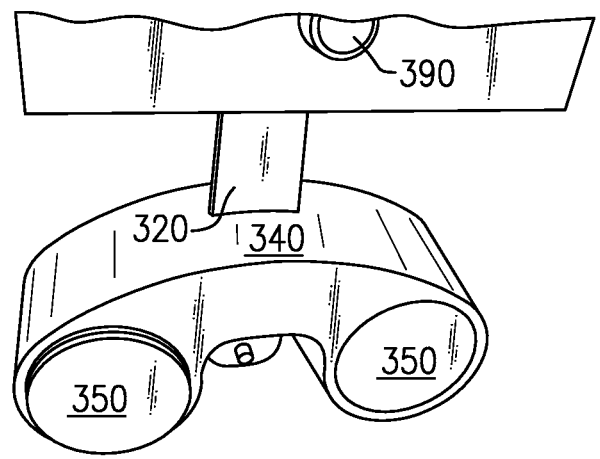
Figure 19D:
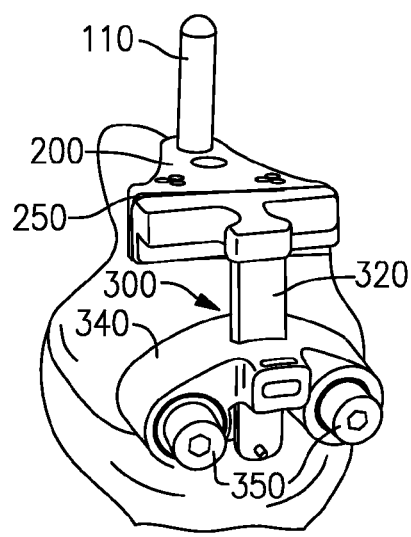

Referring to FIGS. 19A-19D, each cylinder 350 of the adjustable femoral varus/valgus alignment guide 300 (either of the FIG. 1A or 1D embodiments) can be adjusted by engaging the driver engagement features 360 with a tool 361. The actual position of each cylinder 350 is based on the depth of the diseased cartilage (previously determined as known). In other words, the depth of the femoral cut is based on the depth setting of the cylinders 350. The adjustable femoral varus/valgus alignment guide 300 is connected to the cutting surface 250 of the femoral cutting block 200 (FIG. 19D). In one example, the surfaces are magnetically connected. The cutting surface 250 can also include a bore 260 for mating with a corresponding protrusion 359 of the varus/valgus alignment guide 300 to provide additional support for assembling the two components (see FIG. 1B). The guide portion 340 can slide along connecting element 320 (or spaced apart legs 320A and 320B) until the cylinders 350 are aligned with the apex of the femoral condyles or until a desired positioning as determined by a surgeon is otherwise reached.

Figure 20A:
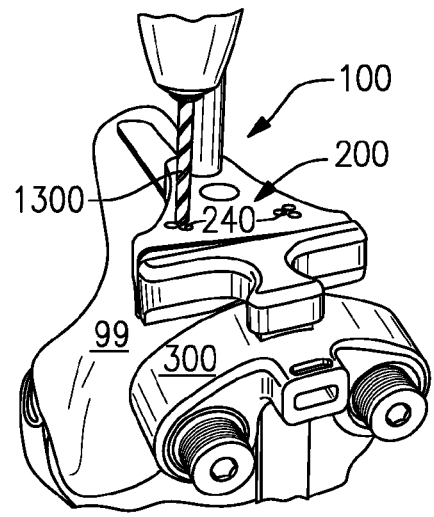
Figure 20B:
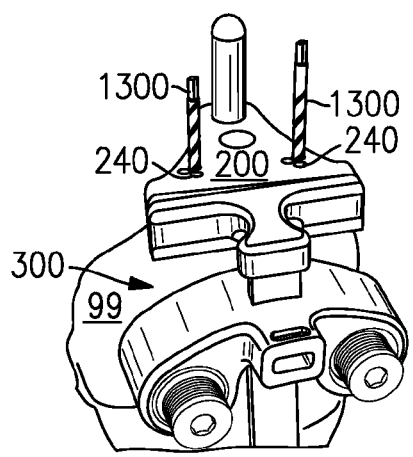
Figure 21A:
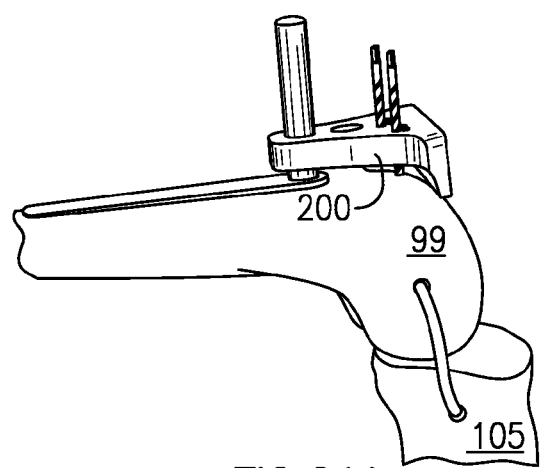
Figure 21B:
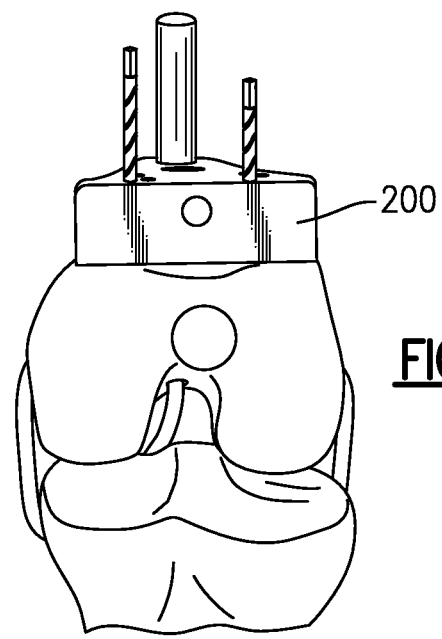
Figure 21C:
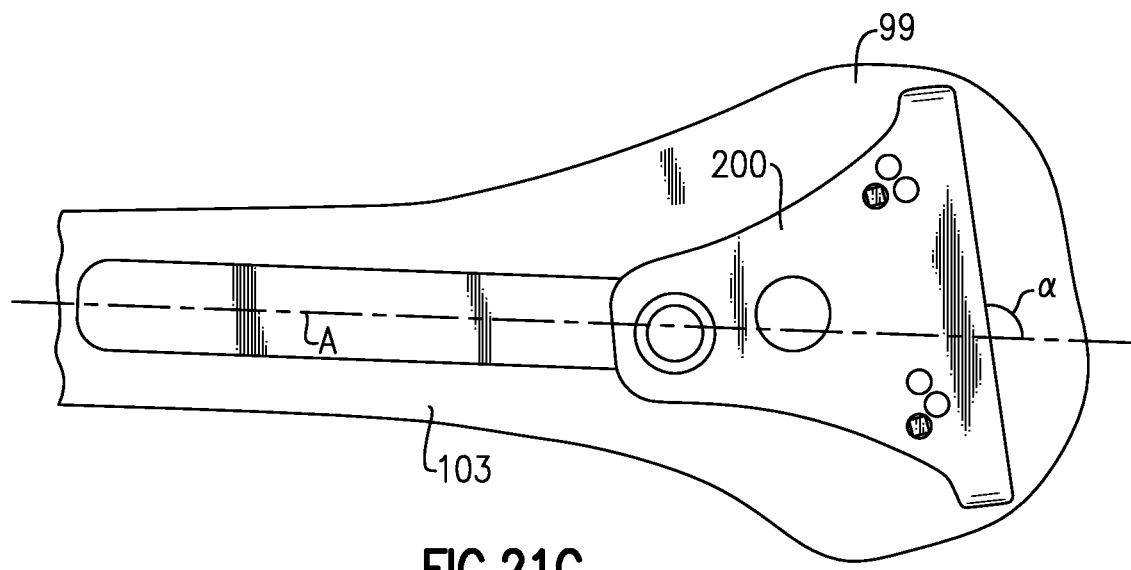

Once the adjustable femoral varus/valgus alignment guide 300 is set at a desired orientation and position, femoral guide pins 1300 are placed through at least two of the pin holes 240 of the femoral cutting block 200 as shown in FIGS. 20A and 20B. Once the femoral guide pins 1300 have been properly positioned into the femur 99, the varus/valgus alignment guide 300 can be disconnected from the femoral cutting block 200 as illustrated in FIGS. 21A (side view), 21B (front view) and 21C (top view). As best demonstrated by FIG. 21C, the femoral cutting block 200 has been positioned at an angle α relative to an axis A of the femoral shaft 103 that approximates an original, pre-disease anatomy of a patient.

Figure 22:
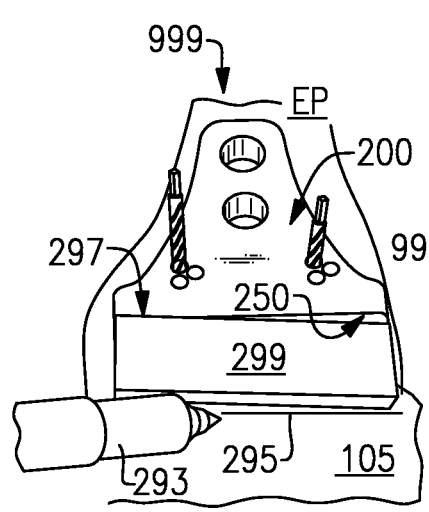
Figure 23:
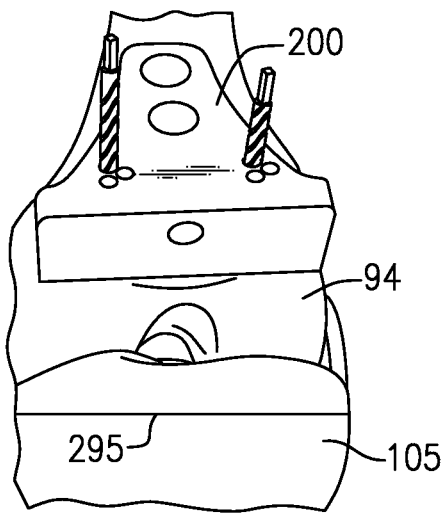

Next, as shown in FIG. 22, the patient's knee 999 can be repositioned to an extended position EP (i.e., the femur 99 and the tibia 105 are coaxial). A marking template 299 can then be positioned to abut the cutting surface 250 of the femoral cutting block 200. A face 297 of the marking template 299 can be magnetic such that the marking template 299 may be magnetically connected to the cutting surface 250 of the femoral cutting block 200. The marking template 299 is used to mark a line 295 on the tibia 105 that denotes a minimum tibial cut depth that is required to accept a total knee implant (see also FIG. 23). The line 295 can be marked with a suitable writing utensil 293, such as a marker.

Figure 24:
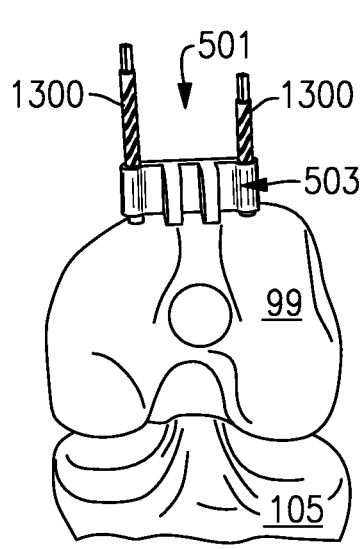
Figure 25:
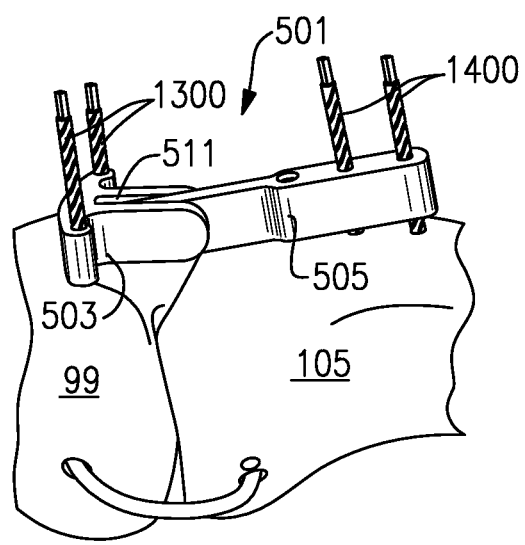

At this point in the procedure, femoral cuts FC can be made in the femur 99 using the femoral cutting block 200 (see FIGS. 10 and 11). Alternatively, as shown in FIG. 24, the femoral cutting block 200 can be removed (without removing the femoral guide pins 1300) and the yoke 503 of the femoral-tibial linkage guide 501 can be placed over the femoral guide pins 1300 to position the yoke 503 on the femur 99. The linkage bar 505 can next be inserted into the groove 511 of the yoke 503 and mounted to the tibia 105 using tibial guide pins 1400 (see FIG. 25).

Figure 26A:
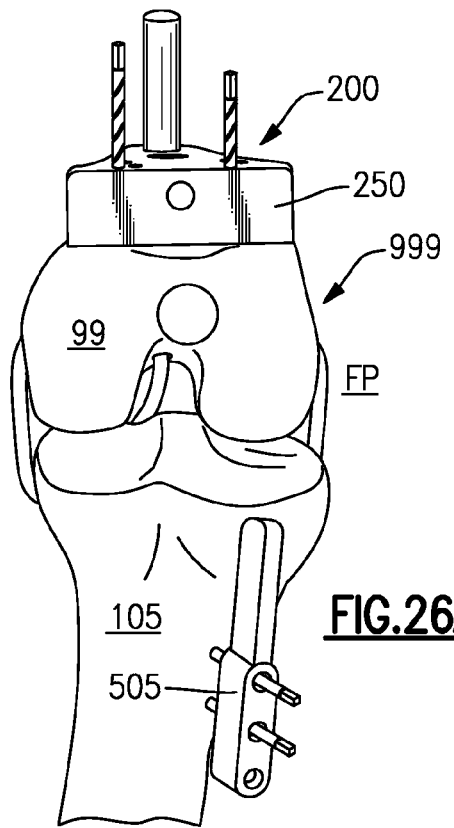
Figure 26B:
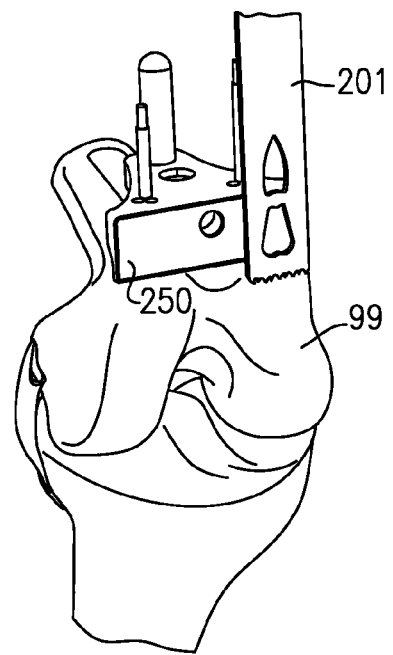
Figure 26C:
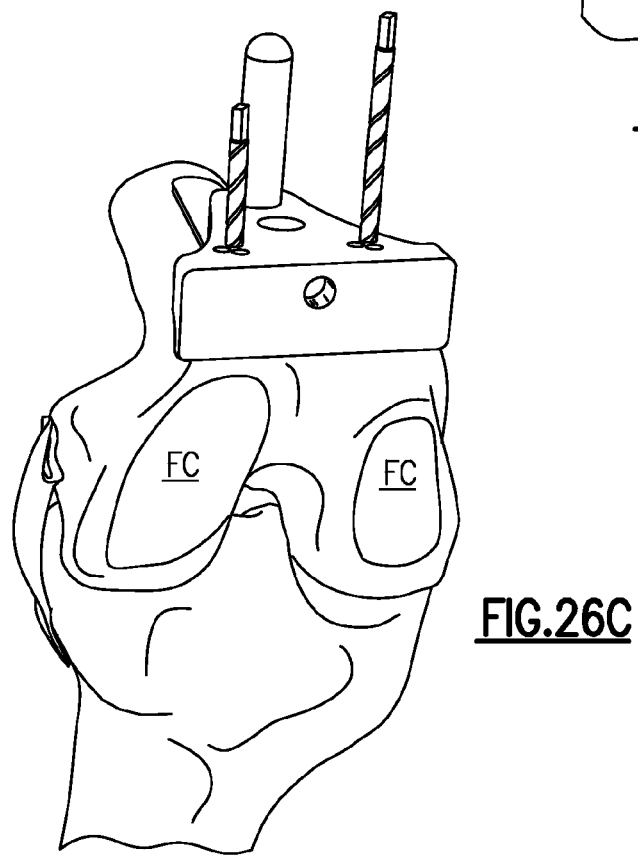

Referring to FIGS. 26A, 26B and 26C, the patient's knee 999 can be repositioned to the flexed position FP. The yoke 503 of the femoral-tibial linkage guide 501 is removed from the femoral guide pins 1300 and can be replaced with the femoral cutting block 200. The linkage bar 505 is left in position on the tibia 105. A cutting tool 201 can then be placed against the cutting surface 250 of the femoral cutting block 200 and used to make the femoral cuts FC (see FIGS. 26B and 26C). In this embodiment, the cutting tool 201 is used to make distal femoral cuts.

Figure 27:
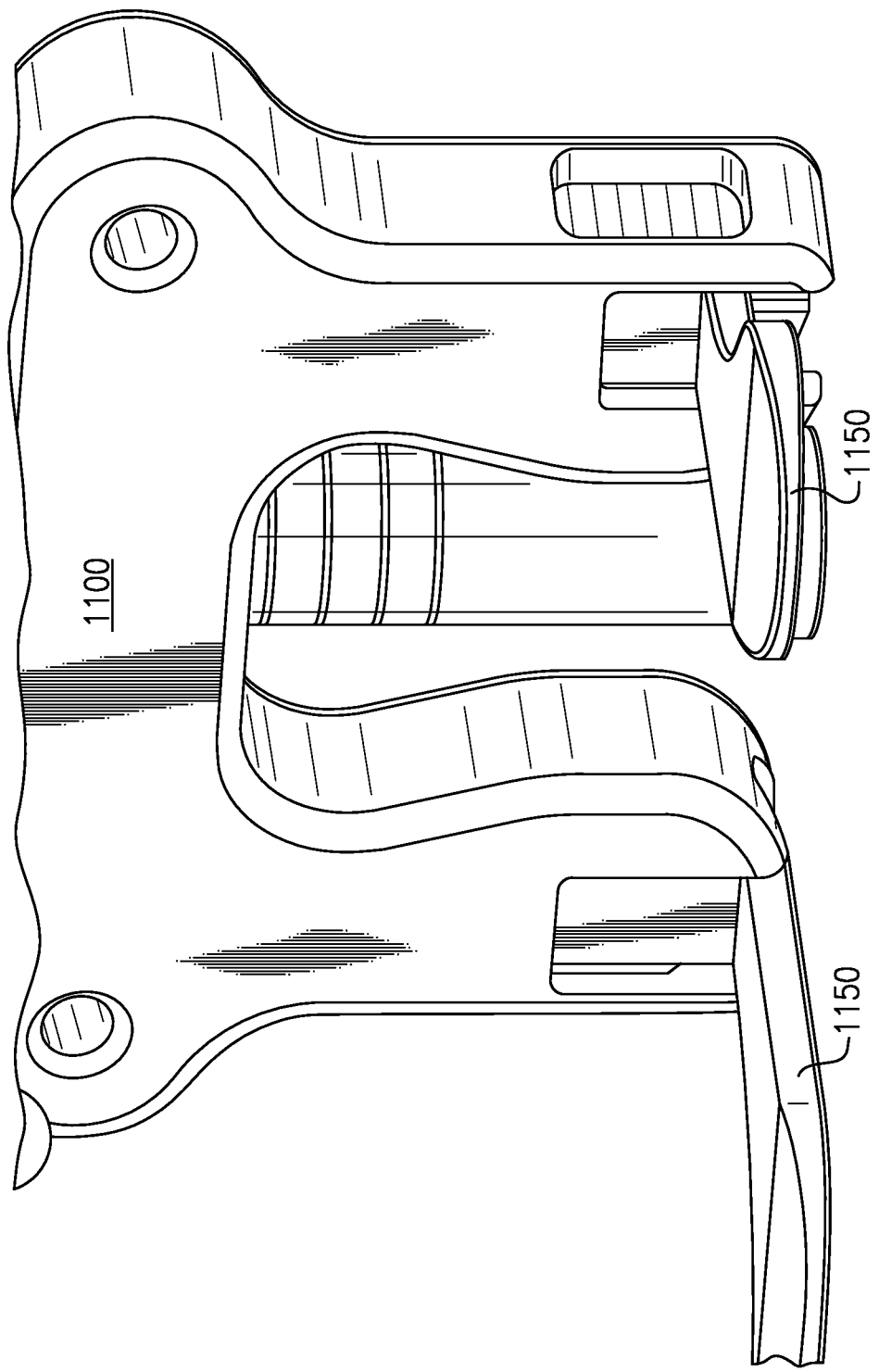

Referring to FIG. 27, the femoral A/P alignment guide 1100, which sets the internal and external rotation of the implant and provides for sizing of the femoral implant, is used to orient and position the femoral anterior, posterior and chamfer cuts. The femoral A/P alignment guide 1100 allows the cuts to be made based on the depth of the diseased cartilage so that removal of healthy bone is minimalized. The femoral A/P alignment guide 1100 has individual feet 1150 that are adjustable to compensate for the depth of the diseased cartilage.

Each foot 1150 is set at a depth that corresponds to an amount of the diseased cartilage in order to restore the patient to his/her original anatomy pre-disease after completion of the total knee implantation. The amount of diseased cartilage is determined by a surgeon. For example, the amount of diseased cartilage can be determined based on measurements from a CT scan, an X-ray, direct visualization and measurement by the surgeon, or any other suitable technique.

Figure 28A:
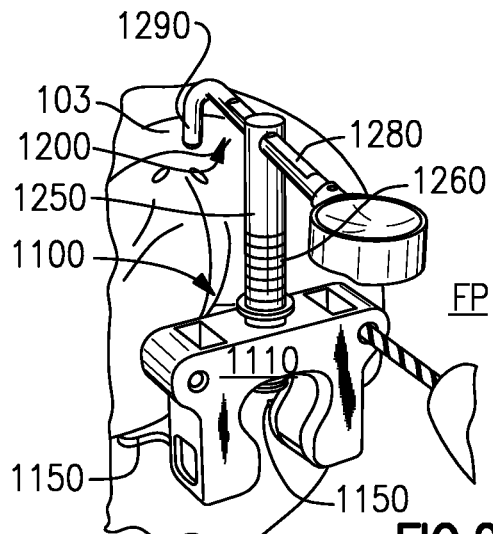

As shown in FIG. 28A, the femoral A/P alignment guide 1100 is placed against the femoral condyles with the knee in the flexed position FP. The hook 1290 of the sizing template 1200 can be extended to contact the femoral shaft 103. Once in the desired position, a size of the femoral implant can be determined by reading the markings 1260 along the sizing rod 1250.

Figure 28B:
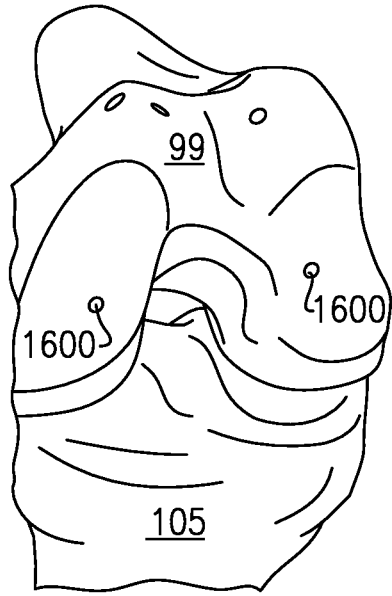

The guide holes 1600 are next drilled through the pin holes 1160 of the base 1110 into the femur 99. The femoral A/P alignment guide 1100 can then be removed (see FIG. 28B).

Figure 29:
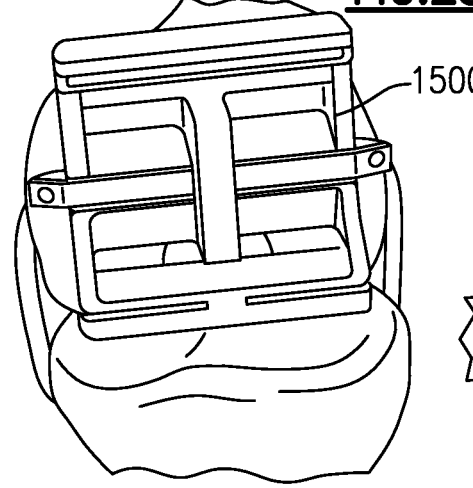
Figure 30:
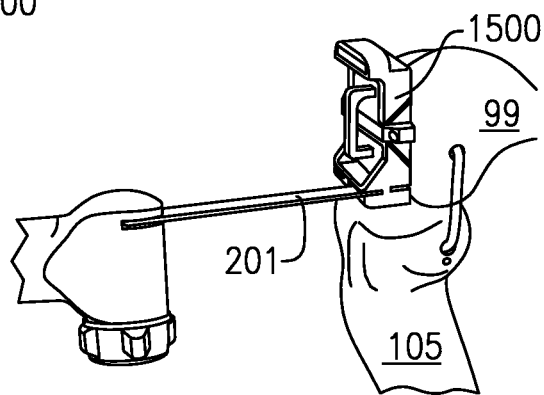

The cutting block 1500 can next be placed in the guide holes 1600 as illustrated in FIG. 29. FIG. 30 illustrates the anterior, posterior and chamfer cuts being made through the cutting block 1500 using a cutting tool 201.

Figure 31:
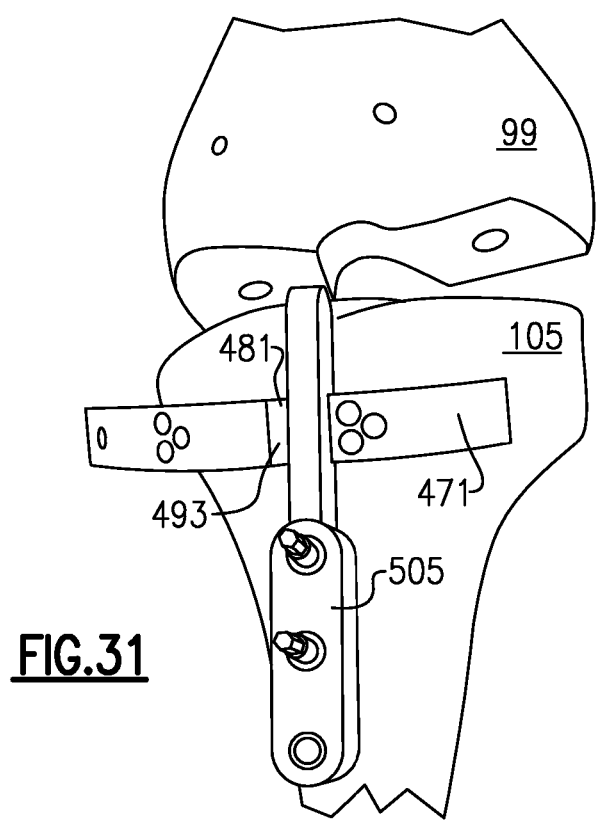

Referring to FIG. 31, the cutting block 1500 is removed from the guide holes 1600 and the cutting block 471 can then be connected to the linkage bar 505. The slot 481 of the cutting block 471 can receive the linkage bar 505 and the positioning between the two parts can be maintained by the spring 493.

Figure 32:
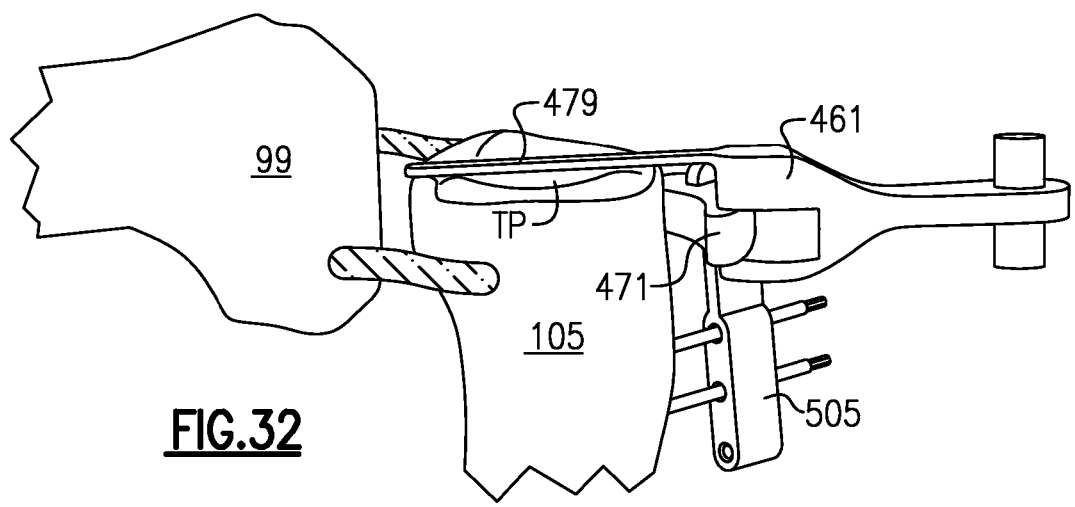
Figure 33A:
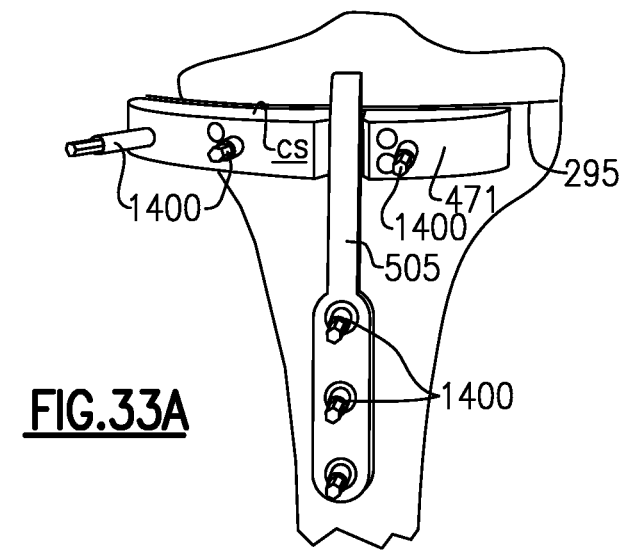
Figure 33B:
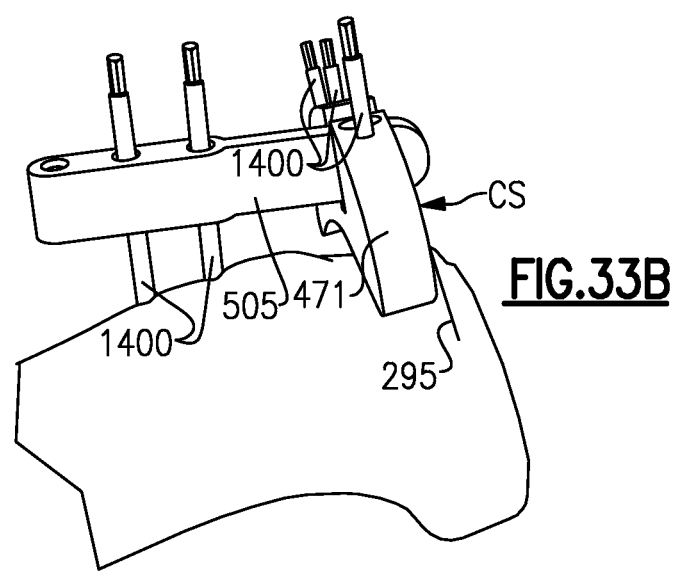

Next, as shown in FIG. 32, the slope indicator 461 can be attached to the cutting block 471 to visually check the anterior/posterior slope alignment and can also be used to set a depth of a bone cut (such as approximately 8 mm distal of the tibial plateau TP, in one example). The second arm 479 may be positioned to rest against the tibial plateau TP of the tibia 105 to aid in the anterior/posterior slope alignment. The slope indicator 461 can be removed once the proper slope alignment has been achieved (see FIG. 33A). The user can then verify whether a cutting surface CS of the cutting block 471 is aligned with the line 295 that was previously marked to identify the minimum depth of the tibial cut. The cutting block 471 can then be secured relative to the tibia 105 with one or more guide pins 1400 (see FIGS. 33A and 33B).

Figure 34A:
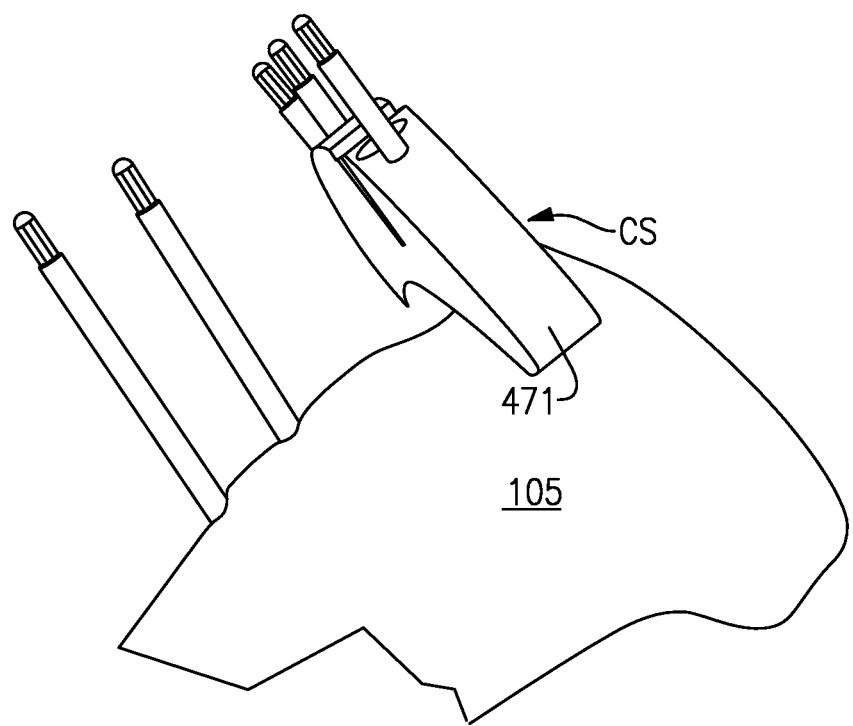
Figure 34B:
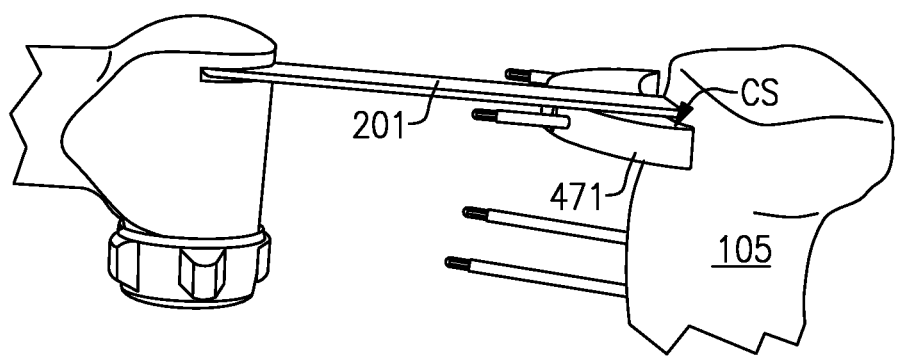

Finally, referring to FIGS. 34A and 34B, the linkage bar 505 can be removed leaving only the cutting block 471 positioned on the tibia 105. A cutting tool 201 can then be used to make a tibial cut by guiding the cutting tool 201 along the cutting surface CS of the cutting block 471. Once all cuts are made, a total knee implant can be implanted as known.

Although the different non-limiting embodiments are illustrated as having specific components, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should also be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:
1. A total joint instrument set, comprising:
 a guide assembly that orients a cut in a first bone, said guide assembly including a femoral alignment guide, a cutting block removably received by said femoral alignment guide and a varus/valgus alignment guide removably connected to said cutting block, and said varus/valgus alignment guide includes a connecting surface that is magnetically connectable to a cutting surface of said cutting block; and a linkage guide that orients a cut in a second bone, wherein a positioning of said linkage guide is mechanically linked to at least a portion of said guide assembly.

2. The total joint instrument set as recited in claim 1, wherein said cutting block is rotatable about a connecting rod of said femoral alignment guide.

3. The total joint instrument set as recited in claim 1, wherein said linkage guide includes a yoke and a linkage bar received by said yoke.

4. The total join instrument set as recited in claim 1, wherein said linkage guide includes a cutting block and a linkage bar received by said cutting block.

5. The total joint instrument set as recited in claim 1, comprising a marking template that aligns said cut in said first bone with said cut in said second bone.

6. The total joint instrument set as recited in claim 1, wherein said linkage guide is mechanically linked to at least one guide pin of said guide assembly.

7. The total joint instrument set as recited in claim 6, wherein said cutting block is removed from said guide assembly prior to mechanically linking said linkage guide.

8. The total joint instrument set as recited in claim 1, wherein said femoral alignment guide includes a connecting rod and an alignment bar that extends from said connecting rod.

9. The total joint instrument set as recited in claim 8, wherein said cutting block is receivable over said connecting rod and is rotatable in a varus/valgus direction about said connecting rod.

10. The total joint instrument set as recited in claim 1, wherein said cutting block includes a plurality of pin holes configured to receive guide pins of said guide assembly.

11. The total joint instrument set as recited in claim 1, wherein said varus/valgus alignment guide includes a guide portion that houses at least one alignment cylinder adjustable to achieve a desired positioning relative to said first bone.

12. The total joint instrument set as recited in claim 11, wherein said at least one alignment cylinder includes a threaded middle section.

13. A total joint instrument set, comprising:
a guide assembly that orients a cut in a first bone;
a linkage guide that orients a cut in a second bone, wherein a positioning of said linkage guide is mechanically linked to at least a portion of said guide assembly;
said linkage guide including a cutting block and a linkage bar received by said cutting block; and
said cutting block including a slot and a spring mounted within a recess of said slot that removably retains said linkage bar within said slot of said cutting block.

14. A total joint instrument set, comprising:
a guide assembly that orients a cut in a first bone;
a linkage guide that orients a cut in a second bone, wherein a positioning of said linkage guide is mechanically linked to at least a portion of said guide assembly;
said linkage guide including a cutting block and a linkage bar received by said cutting block; and a slope indicator removably connected to said cutting block to adjust an anterior/posterior slope alignment in said second bone.

15. A total joint instrument set, comprising:
a guide assembly that orients a cut in a first bone, said guide assembly including a femoral alignment guide, a cutting block removably received by said femoral alignment guide and a varus/valgus alignment guide removably connected to said cutting block;
a linkage guide that orients a cut in a second bone, wherein a positioning of said linkage guide is mechanically linked to at least a portion of said guide assembly;
said femoral alignment guide includes a connecting rod and an alignment bar that extends from said connecting rod; and
said alignment bar is sized and shaped to extend along a shaft of said first bone and extends transversely from said connecting rod.

16. A total joint instrument set, comprising:
a guide assembly that orients a cut in a first bone, said guide assembly including a femoral alignment guide, a cutting block removably received by said femoral alignment guide and a varus/valgus alignment guide removably connected to said cutting block;
a linkage guide that orients a cut in a second bone, wherein a positioning of said linkage guide is mechanically linked to at least a portion of said guide assembly; and
said cutting block includes a cutting surface having one of a bore and a protrusion and said varus/valgus alignment guide includes the other of said bore and said protrusion for connecting said varus/valgus alignment guide to said cutting block.

17. A total joint instrument set, comprising:
a guide assembly that orients a cut in a first bone, said guide assembly including a femoral alignment guide, a cutting block removably received by said femoral alignment guide and a varus/valgus alignment guide removably connected to said cutting block;
a linkage guide that orients a cut in a second bone, wherein a positioning of said linkage guide is mechanically linked to at least a portion of said guide assembly;
said varus/valgus alignment guide includes a guide portion that houses at least one alignment cylinder adjustable to achieve a desired positioning relative to said first bone; and
said guide portion houses at least two alignment cylinders that are independently turnable to adjust said at least two alignment cylinders in the anterior/posterior directions.

18. A total joint instrument, comprising:
a guide assembly that orients a cut in a femur, said guide assembly including a cutting block having a cutting surface, a varus/valgus alignment guide magnetically connectable to said cutting surface, and at least one guide pin that extends through said cutting block and into said femur; and
a linkage guide that orients a cut in a tibia, said linkage guide connectable to said at least one guide pin after removing said cutting block.

* * * * *